(12) United States Patent
Tan et al.

(10) Patent No.: US 8,645,082 B2
(45) Date of Patent: Feb. 4, 2014

(54) MONITORING, DETECTING AND QUANTIFYING CHEMICAL COMPOUNDS IN A SAMPLE

(75) Inventors: Huwei Tan, Burlington, MA (US); Svante Bjarne Wold, Hollis, NH (US)

(73) Assignee: MKS Instruments, Inc., Andover, MA (US)

( * ) Notice: Subject to any disclaimer, the term of this patent is extended or adjusted under 35 U.S.C. 154(b) by 673 days.

(21) Appl. No.: 12/880,903

(22) Filed: Sep. 13, 2010

(65) Prior Publication Data
US 2012/0065948 A1     Mar. 15, 2012

(51) Int. Cl.
*G01N 31/00* (2006.01)
(52) U.S. Cl.
USPC .......................................................... 702/27
(58) Field of Classification Search
USPC .......................................................... 702/27
See application file for complete search history.

(56) References Cited

U.S. PATENT DOCUMENTS

| | | | |
|---|---|---|---|
| 6,528,809 | B1 | 3/2003 | Thomas et al. |
| 6,748,334 | B1 | 6/2004 | Perez et al. |
| 7,956,761 | B2 | 6/2011 | Polak et al. |
| 2002/0158212 | A1* | 10/2002 | French et al. ............... 250/459.1 |
| 2003/0154044 | A1 | 8/2003 | Lundstedt et al. |
| 2004/0082070 | A1 | 4/2004 | Jones et al. |
| 2004/0124357 | A1 | 7/2004 | Leu et al. |
| 2010/0090845 | A1* | 4/2010 | Polak et al. .................... 340/632 |
| 2010/0223015 | A1 | 9/2010 | Phillips et al. |

OTHER PUBLICATIONS

Wold, S., "Exponentially weighted moving principal components analysis and projections to latent structures," *Chemometrics and Intelligent Laboratory Systems*, 23:149-161 (1994).
The International Search Report for PCT Application No. PCT/US2011/050887, mailed on Dec. 9, 2011 (4 pgs.).

* cited by examiner

*Primary Examiner* — Aditya Bhat
(74) *Attorney, Agent, or Firm* — Proskauer Rose LLP

(57) ABSTRACT

Described are computer-based methods and apparatuses, including computer program products, for monitoring, detecting, and quantifying chemical compounds in a sample. A sample measurement comprising a digitized spectroscopic profile is received. A multivariate multistage background model comprising a first model that models a first time effect, a second model that models a second time effect that is different than the first time effect, or both is calculated. A background corrected sample measurement based on the sample measurement and the multivariate multistage background model is generated. A multivariate multistage library search, fault detection, and quantification algorithm is executed to identify one or more primary chemicals in the background corrected sample measurement. The search, detection, and quantification algorithm includes identifying one or more candidate chemicals in the background corrected sample measurement based on a multivariate statistical process control and identifying and quantifying a first primary chemical based on a focused chemical evaluation of the one or more candidate chemicals.

12 Claims, 13 Drawing Sheets

MONITORING, DETECTING AND QUANTIFYING CHEMICAL COMPOUNDS IN A SAMPLE

FIELD OF THE INVENTION

The invention generally relates to monitoring, detecting, and quantifying chemical compounds in a sample, and specifically to monitoring a continuous air or liquid stream by a spectroscopic method for the purpose of rapidly detecting and quantifying a range of specific chemical materials in stream samples at low concentrations.

BACKGROUND

Spectroscopy is the study of the interaction between electromagnetic radiation and a sample (e.g., containing one or more of a gas, solid and liquid). The manner in which the radiation interacts with a particular sample depends upon the properties (e.g., molecular composition) of the sample. Generally, as the radiation passes through the sample, specific wavelengths of the radiation are absorbed by chemical compounds within the sample. The specific wavelengths of radiation that are absorbed are unique to each of the chemical compounds within the specific sample. By identifying which wavelengths of radiation are absorbed, it is therefore possible to identify the specific chemical compounds present in the sample.

Infrared spectroscopy is a particular field of spectroscopy in which, for example, the types of chemical compounds and the concentration of individual chemical compounds within a sample are determined by subjecting the sample (e.g., gas, solid, liquid or combination thereof) to infrared electromagnetic energy. Generally, infrared energy is characterized as electromagnetic energy having wavelengths of energy between about 0.7 μm (frequency 14,000 $cm^{-1}$) and about 1000 μm (frequency 10 $cm^{-1}$). Infrared energy is directed through the sample and the energy interacts with the chemical compounds within the sample. The energy that passes through the sample is detected by a detector (e.g., an electromagnetic detector). The detected signal is then used to determine, for example, the molecular composition of the sample and the concentration of specific chemical compounds within the sample.

For infrared spectroscopy, the infrared absorbance spectrum can be linked to chemical concentrations by mathematical equations (e.g., Beer's Law, which relates the absorption of light to the properties of the material through which the light is traveling). A critical variable in these equations is the "background spectrum" (or "background spectra"), which can be used as a baseline from which to detect and quantify new chemical compounds. The background spectrum is often calculated to quantify the infrared source that is being passed through the sample of interest. The background spectrum can also account for other instrument functions and environmental conditions. For example, the background spectrum can be measured in a clean environment before a sample of interest is introduced to the system, such that new measurements are compared against the background spectrum. Advantageously, the system can ignore the background chemical compounds and other background components (identified using the background spectrum) and only monitor and/or detect and quantify new (or additional) chemical compounds.

The background spectrum is often approximated by a single background spectrum (e.g., a constant background spectrum that does not compensate for changes over time, such as changes to the instrument and/or the environment). Ideally, when the instrument's stability and environmental conditions are well controlled, the actual background spectra should be a constant vector over time that is sufficiently close enough to the background spectrum such that the error is white and negligible (and the chemical identification and quantification of new chemical compounds can be implemented with acceptable accuracy and precision). However, the instrument and/or the environment often change so frequently that a single background spectrum does not accurately model the true background of the system. This can lead to inaccurate and/or erroneous chemical compound detections (e.g., false positives or missed chemical compound detections).

SUMMARY OF THE INVENTION

Spectroscopy can be used to detect, identify, and/or quantify trace amounts of chemical compounds (or compounds) in a sample. Concentrations of chemical compounds can be measured in-situ (e.g., at the site of, for example a building, tunnel, landfill) and in real time (e.g., immediately and rapidly processing and analyzing the content of the sample at a site without having to obtain a sample and analyze the sample at a laboratory at a relatively later point in time). In some embodiments described herein, a multivariate multistage background algorithm is calculated, including a first model (e.g., an evolving background model) and a second model (e.g., a multivariate noise model) that models the remaining noise in the evolution background model. The multivariate multistage background algorithm is applied to sample measurements (e.g., digitized sample spectra) to generate a background corrected sample spectrum. In some embodiments described herein, a multivariate multistage library search, fault detection, and quantification algorithm is applied to the background corrected sample spectrum to identify one or more candidate chemicals (with a fault detection algorithm), and to calculate the concentrations of one or more primary chemicals of interest in the list of the one or more candidate chemicals (using a multivariate library search).

The invention, in one aspect, features a computerized method for detecting and quantifying chemicals in a continuously sampled liquid or gas sample stream. The method includes receiving, by a computing device, a sample measurement including a digitized spectroscopic profile. The method includes calculating, by the computing device, a multivariate multistage background model including a first model that models a first time effect, a second model that models a second time effect that is different than the first time effect, or both. The method includes generating, by the computing device, a background corrected sample measurement based on the sample measurement and the multivariate multistage background model. The method includes executing, by the computing device, a multivariate multistage library search, fault detection, and quantification algorithm to identify one or more primary chemicals in the background corrected sample measurement. The algorithm includes identifying one or more candidate chemicals in the background corrected sample measurement based on a multivariate statistical process control in comparison of the background corrected sample measurement to a spectral reference library. The algorithm includes performing at least one of (i) identifying a first primary chemical based on a focused chemical evaluation of the one or more candidate chemicals or (ii) quantifying the first primary chemical based on the focused chemical evaluation of the one or more candidate chemicals.

The invention, in another aspect, features a system for detecting and quantifying chemicals in a continuously sampled liquid or gas sample stream. The system includes a data acquisition module configured to receive a sample measurement including a digitized spectroscopic profile. The system includes a multivariate multistage background module in communication with the data acquisition module configured to calculate a multivariate multistage background model including at least a first model that models a first time effect and a second model that models a second time effect that is different than the first time effect. The multivariate multistage background module is configured to generate a background corrected sample measurement based on the sample measurement and the multivariate multistage background model. The multivariate multistage background module is configured to update the multivariate multistage background model based on the sample measurement. The system includes a data quality diagnostic module in communication with the multivariate multistage background module configured to determine the sample measurement is suitable for inclusion as an update to the multivariate multistage background model.

The invention, in another aspect, features a computer program product, tangibly embodied in a computer readable storage medium. The computer program product includes instructions being operable to cause a data processing apparatus to receive a sample measurement including a digitized spectroscopic profile. The computer program product further includes instructions being operable to cause a data processing apparatus to calculate a multivariate multistage background model including a first model that models a first time effect, a second model that models a second time effect that is different than the first time effect, or both. The computer program product further includes instructions being operable to cause a data processing apparatus to generate a background corrected sample measurement based on the sample measurement and the multivariate multistage background model. The computer program product further includes instructions being operable to cause a data processing apparatus to execute a multivariate multistage library search, fault detection, and quantification algorithm to identify one or more primary chemicals in the background corrected sample measurement. The algorithm is configured to identify one or more candidate chemicals in the background corrected sample measurement based on a multivariate statistical process control in comparison of the background corrected sample measurement to a spectral reference library. The algorithm is configured to identify a first primary chemical based on a focused chemical evaluation of the one or more candidate chemicals.

The invention, in another aspect, features a computer program product, tangibly embodied in a computer readable storage medium. The computer program product includes instructions being operable to cause a data processing apparatus to repeatedly execute a multivariate multistage library search, fault detection, and quantification algorithm to identify one or more primary chemicals in a sample measurement when a candidate chemical of the sample measurement is greater than a predetermined threshold, the sample measurement including a digitized spectroscopic profile. The algorithm is configured to identify one or more candidate chemicals in a sample measurement based on a comparison of the sample measurement to a spectral reference library. The algorithm is configured to identify a primary chemical of the one or more primary chemicals from the one or more candidate chemicals based on a focused chemical evaluation of the one or more candidate chemicals. The algorithm is configured to determine whether any of the remaining one or more candidate chemicals are greater than the predetermined threshold.

The invention, in another aspect, features a computer program product, tangibly embodied in a computer readable storage medium. The computer program product includes instructions being operable to cause a data processing apparatus to receive a sample measurement including a digitized spectroscopic profile. The computer program product includes instructions being operable to cause a data processing apparatus to calculate a multivariate multistage background model including at least a first model that models a first time effect and a second model that models a second time effect that is different than the first time effect. The computer program product includes instructions being operable to cause a data processing apparatus to generate a background corrected sample measurement based on the sample measurement and the multivariate multistage background model. The computer program product includes instructions being operable to cause a data processing apparatus to determine the sample measurement is suitable for inclusion as an update to the multivariate multistage background model. The computer program product includes instructions being operable to cause a data processing apparatus to update the multivariate multistage background model based on the sample measurement.

The invention, in another aspect, features a system for detecting and quantifying chemicals in a continuously sampled liquid or gas sample stream. The system includes a data acquisition module configured to receive a sample measurement including a digitized spectroscopic profile. The system includes a multivariate multistage background module in communication with the data acquisition module configured to calculate a multivariate multistage background model including a first model that models a first time effect, a second model that models a second time effect that is different than the first time effect, or both. The multivariate multistage background module is configured to generate a background corrected sample measurement based on the sample measurement and the multivariate multistage background model. The system includes a multivariate multistage library search, fault detection, and quantification module in communication with the data acquisition module and the multivariate multistage background module configured to execute a multivariate multistage library search, fault detection, and quantification algorithm to identify one or more primary chemicals in the background corrected sample measurement. The multivariate multistage library search, fault detection, and quantification module is configured to identify one or more candidate chemicals in the background corrected sample measurement based on a comparison of the background corrected sample measurement to a spectral reference library. The multivariate multistage library search, fault detection, and quantification module is configured to perform at least one of (i) identifying a first primary chemical based on a focused chemical evaluation of the one or more candidate chemicals or (ii) quantifying the first primary chemical based on the focused chemical evaluation of the one or more candidate chemicals.

The invention, in another aspect, features a computerized method for detecting and quantifying chemicals in a continuously sampled liquid or gas sample stream. The computerized method includes repeatedly executing, by the computing device, a multivariate multistage library search, fault detection, and quantification algorithm to identify one or more primary chemicals in a sample measurement when a candidate chemical of the sample measurement is greater than a predetermined threshold, the sample measurement including a digitized spectroscopic profile. The multistage library search, fault detection, and quantification algorithm includes identifying one or more candidate chemicals in a sample measurement based on a comparison of the sample measurement to a spectral reference library. The multistage library search, fault detection, and quantification algorithm includes identifying a primary chemical of the one or more primary chemicals from the one or more candidate chemicals based on a focused chemical evaluation of the one or more candidate chemicals. The multistage library search, fault detection, and quantification algorithm includes determining whether any of the remaining one or more candidate chemicals are greater than the predetermined threshold.

The invention features, in another aspect, a system for detecting and quantifying chemicals in a continuously sampled liquid or gas sample stream. The system includes a multivariate multistage library search, fault detection, and quantification module in communication with the data acquisition module and the multivariate multistage background module configured to repeatedly execute a multivariate multistage library search, fault detection, and quantification algorithm to identify one or more primary chemicals in a sample measurement when a candidate chemical of the sample measurement is greater than a predetermined threshold, the sample measurement including a digitized spectroscopic profile. The multivariate multistage library search, fault detection, and quantification module includes a fault detection module configured to identify one or more candidate chemicals in a sample measurement based on a comparison of the sample measurement to a spectral reference library. The multivariate multistage library search, fault detection, and quantification module includes a library search module in communication with the fault detection module configured to identify a first primary chemical from the one or more candidate chemicals based on a focused chemical evaluation of the one or more candidate chemicals, and determine whether any of the remaining one or more candidate chemicals are greater than the predetermined threshold.

The invention features, in another aspect, a computerized method for detecting and quantifying chemicals in a continuously sampled liquid or gas sample stream. The method includes receiving, by a computing device, a sample measurement including a digitized spectroscopic profile. The method includes calculating, by the computing device, a multivariate multistage background model including at least a first model that models a first time effect and a second model that models a second time effect that is different than the first time effect. The method includes generating, by the computing device, a background corrected sample measurement based on the sample measurement and the multivariate multistage background model. The method includes determining, by the computing device, the sample measurement is suitable for inclusion as an update to the multivariate multistage background model. The method includes updating, by the computing device, the multivariate multistage background model based on the sample measurement.

In other examples, any of the aspects above can include one or more of the following features. Identifying the first primary chemical can include determining there are zero primary chemicals. Calculating can include updating the multivariate multistage background model. The multivariate multistage library search, fault detection, and quantification algorithm can further include calculating a residual profile by subtracting the first primary chemical from the background corrected sample measurement, quantifying content by estimating the first primary chemical concentration from the background corrected sample measurement, identifying a second set of one or more candidate chemicals in the residual profile based on a comparison of the residual profile to the spectral reference library, and identifying a second primary chemical based on a focused chemical evaluation of the second set of one or more candidate chemicals.

In some examples, the sample measurement is determined to be suitable for inclusion into the multivariate multistage background model, and the multivariate multistage background model is updated based on the sample measurement. The sample measurement can be filtered through a data buffer to prevent contamination resulting from slow chemical data poisoning in the sample stream. A size of the data buffer can be determined based on a data poisoning rate value.

In other examples, an influence of one or more interference chemicals in the sample measurement is reduced based on a mask function. One or more chemical interferents can be identified, and the mask function can be updated based on one or more identified chemical interferents. One or more update conditions can be defined, including updating at least one of (i) the multivariate multistage background model or (ii) the multivariate multistage library search, fault detection, and quantification model, if zero chemical compounds are detected in the sample measurement, updating at least one of (i) the multivariate multistage background model or (ii) the multivariate multistage library search, fault detection, and quantification model, if zero interest chemical compounds are detected in the sample measurement, updating at least one of (i) the multivariate multistage background model or (ii) the multivariate multistage library search, fault detection, and quantification model, if there is no alarm of any interest chemical compounds in the sample measurement, or not updating at least one of (i) the multivariate multistage model or (ii) the multivariate multistage library search, fault detection, and quantification model.

In some examples, identifying a primary chemical includes determining there are zero primary chemicals. The sample measurement can be a background corrected sample measurement calculated based on a multivariate multistage background model. The one or more candidate chemicals can be identified based on a matrix-based simultaneous comparison including a least squares regression. The least squares regression can include classical least squares, partial least squares, inverse least squares, or any combination thereof. The one or more candidate chemicals can be identified based on a multivariate regression. The primary chemical of the one or more primary chemicals can be identified based on a least squares regression.

In other examples, identifying the primary chemical of the one or more primary chemicals includes calculating a root mean square of a digitized spectrum of each of the one or more candidate chemicals, calculating a concentration of each of the one or more candidate chemicals, calculating a t-statistic of the digitized spectra of each of the one or more candidate chemicals, wherein the t-statistic is based on a variance of the associated candidate chemical of the one or more candidate chemicals, and identifying the first primary chemical primary chemical from the one or more candidate chemicals, wherein the first primary chemical includes a lowest root mean square and highest t-statistic of the one or more candidate chemicals.

In some examples, the spectral reference library is constant, the spectral reference library is dynamically updated to include or exclude spectra, or both. The spectral reference library can be dynamically augmented with a multivariate noise model. The first model of the multivariate multistage background model can include an evolving background model. A background spectrum of the evolving background model can be initiated in a time domain, a frequency domain, or both, based on an exponentially weighted moving average, and the background spectrum can be updated based on the exponentially weighted moving average. The second model of the multivariate multistage background algorithm can include a multivariate noise model.

In other examples, the multivariate noise model is filtered based on the first model, and a remaining spectral variation of the multivariate noise model is corrected based on a multivariate approach includes principal components analysis, independent components analysis, multivariate curve resolution, partial least squares, weighted least squares, total least squares, continuum regression, ridge regression, or any combination thereof.

In some examples, the multivariate noise model is updated based on an exponentially weighted multivariate approach to minimize a residual profile of the corrected remaining spectral variation, wherein the exponentially weighted multivariate approach includes exponentially weighted moving principal components analysis, exponentially weighted moving independent components analysis, exponentially weighted moving multivariate curve resolution, exponentially weighted moving partial least squares, exponentially weighted moving total least squares, exponentially weighted moving continuum regression, exponentially weighted moving ridge regression, or any combination thereof.

The techniques, which include methods and apparatuses, described herein can provide one or more of the following advantages. Advantageously, a multistage background model (which can be frequently updated) can greatly decrease the systematic and spectral variation of the detection system (e.g., compared to using just a single background spectrum). The multistage background model (e.g., including a first background model such as an evolving background model and a second background model such as a multivariate noise model) allows measurements (e.g. infrared measurements) to be calculated over a long period time. The multistage background model can be updated with background data to follow the drift of the instrument and/or the environment. A time delay can be applied to the background data to prevent the multistage background model and/or a fault detection model from being contaminated by the signal which contain threat chemicals or gases of interest. The first background model (e.g., an averaged background model) can be computed as both an interferogram in the time domain and a spectrum in the frequency domain. A multi-threaded architecture can allow the system to apply the multistage background model in real-time while model updates (or portions thereof, such as updates to the second model) are calculated using background processes.

A multivariate multistage library search, fault detection, and quantification can be applied to the background-corrected measurements. The first stage generates a list of candidate chemicals that are highly recommended for further processing by the second stage using a digitized spectral reference library. Advantageously, the first stage can quickly identify one or more candidate chemicals, and the second stage can then determine whether or not each of the candidate chemicals should be identified as a chemical of interest as well as the calculated concentration of each identified chemical. Other aspects and advantages of the present invention will become apparent from the following detailed description, taken in conjunction with the accompanying drawings, illustrating the principles of the invention by way of example only.

The multistage library search, fault detection, and quantification algorithm includes a chemical prescreening and refining. Advantageously, this can allow for a quick implementation of chemical identification and quantification for a large scale library. Combining a multistage background model and a multistage library search, fault detection, and quantification improves the sensitivity (detection limit), without losing speed of algorithm implementation.

BRIEF DESCRIPTION OF THE DRAWINGS

The foregoing and other aspects, features, and advantages of the present invention, as well as the invention itself, will be more fully understood from the following description of various embodiments, when read together with the accompanying drawings.

DETAILED DESCRIPTION

Figure 1:
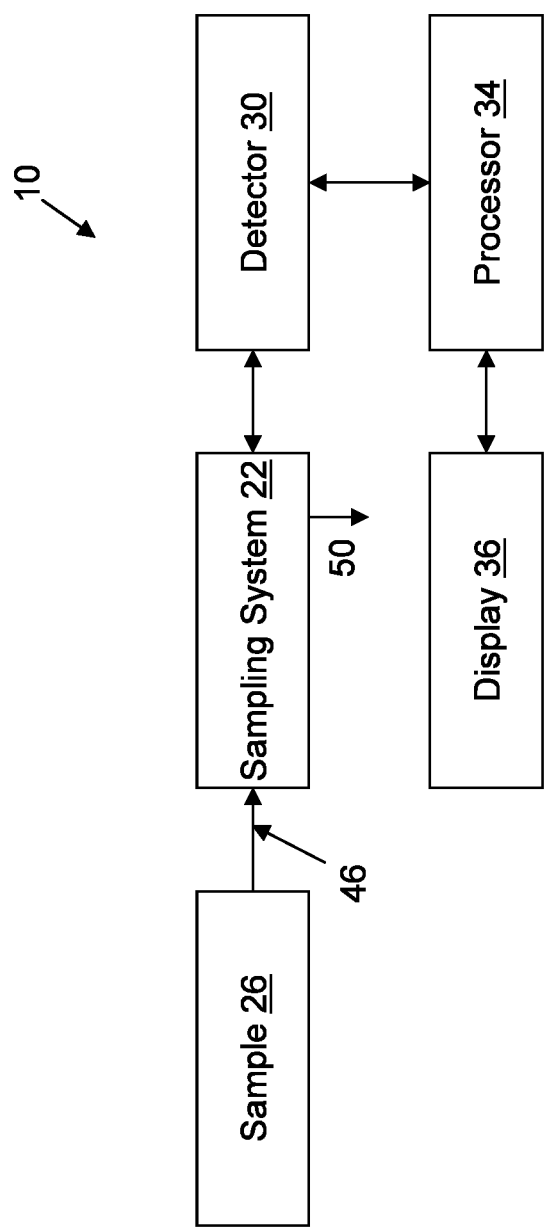
FIG. 1 illustrates an exemplary block diagram of a detection system for monitoring and/or detecting and quantifying chemical compounds in a sample.

In general, chemicals at trace or low level concentrations are detected and quantified by analyzing, using a computer program, spectral data from a continuously sampled liquid or gas sample stream. The terms "spectra" and "digitized spectra" can be used interchangeably to refer to digitized spectral information. The computer program comprises a multistage background algorithm, a multistage fault detection, library search, and quantification algorithm, and a data quality diagnostic module.

The multivariate multistage background algorithm models systemic and/or environmental variations observed in spectral profiles over time. The multivariate multistage background algorithm can precisely and dynamically describe the instrument function and environmental conditions. The multivariate multistage background algorithm includes, for example, a first model (e.g., an evolving background model) and a second model (e.g., a multivariate noise model) that models the remaining noise in the first model. The multivariate multistage background algorithm is referred to as being "multivariate" because the approach, in some embodiments, can apply to multivariate spectral profiles (which are multivariate and not univariate measurements). The multivariate multistage background algorithm is referred to as being "multistage" because the algorithm can include one or more stages to generate the background model. For example, the background algorithm can include a stage to calculate the first model to model the background. In some examples, the background algorithm includes a stage (either separate from or in addition to other stages) to calculate the second model to account for noise that is not modeled by the first model. The system applies the multivariate multistage background algorithm to sample measurements to generate a background corrected sample spectrum. The multivariate multistage background algorithm is often referred to herein as a "background algorithm" for abbreviation.

A multivariate multistage library search, fault detection, and quantification algorithm is applied to the background corrected sample spectrum to calculate the probability of the presence of one or more chemicals of interest. The multivariate multistage library search, fault detection, and quantification algorithm comprises a multivariate fault detection algorithm and a spectral residual analysis, capable of quickly recognizing and quantifying a broad range of chemical compounds at trace levels, while referencing a large computerized library of spectra of pertinent chemicals. The multivariate multistage library search, fault detection, and quantification algorithm is referred to as being "multivariate" because the approach, in some embodiments, can apply to multivariate spectral profiles. The multivariate multistage library search, fault detection, and quantification algorithm is referred to as being "multistage" because the algorithm can include one or more stages to identify the chemicals of interest as well as the calculated concentration of each identified chemical. For example, the library search, fault detection, and quantification algorithm can include a first stage to calculate one or more candidate chemicals from the background corrected sample measurement (e.g., based on control charts generated using spectral reference library). In some examples, the library search, quantification, and fault detection algorithm can include a second stage to determine and refine the one or more chemicals of interest based on the one or more candidate chemicals (e.g., based on residuals, t-values, an/or concentrations). The multivariate multistage library search, fault detection, and quantification algorithm is often referred to herein as a "search, detection, and quantification algorithm" for abbreviation.

The data quality diagnostic module screens the current sample measurement for data integrity prior to library search, fault detection, and quantitative analysis. The data quality diagnostic module also qualifies the sample for inclusion in the background algorithm, and further filters the background through a data buffer to prevent background contamination resulting from slow chemical poisoning in the sample stream. The computer program uses a multithread architecture to quickly analyze the sample measurements in real-time while remaining capable of dynamically updating the more complex multivariate models in a background-type process.

Although the specification and/or figures describe(s) the techniques in terms of applying a background algorithm to generate a background corrected sample spectrum and using a search, detection, and quantification algorithm to analyze the corrected sample spectrum, these techniques do not require the algorithms to be used in conjunction. In some embodiments, only the background algorithm is used to generate the background corrected sample spectrum (e.g., a different algorithm is used to detect faults). In some embodiments, only the search, detection, and quantification algorithm is used to detect faults (e.g., the search, detection, and quantification algorithm is applied to an uncorrected sample measurement, an evolving background corrected sample measurement, or another background generated by a different background correction algorithm).

FIG. 1 illustrates an exemplary block diagram of a detection system for monitoring, detecting, and/or quantifying chemical compounds in a sample (e.g., for monitoring a trace gas in a gas sample). The detection system 10 can be used to detect and quantify trace amounts of substances such as, for example, sarin, tabun, soman, sulfur mustard, and VX nerve gas. In some embodiments, vapors of a solid or liquid substance can be detected and quantified. The detection system 10 can be, for example, an absorption spectrometer and/or can be a Fourier Transform spectroscopy e.g., optical spectroscopy, infrared spectroscopy (FTIR, FT-NIRS, FT-Raman), nuclear magnetic resonance (NMR) and magnetic resonance spectroscopic imaging (MRSI), mass spectrometry and electron spin resonance spectroscopy, etc In some embodiments, the FT spectroscopy can be the AIRGARD® air analyzer provided by MKS Instruments, Inc. (Wilmington, Mass.), which is designed to rapidly detect and quantify chemical agents and toxic industrial chemicals (TICs) at part-per-billion (ppb) concentration levels. In the embodiment illustrated, the detection system 10 includes a source for a gas sample 26, a measurement unit 27, a detector 30, a processor 34, and a display 38. In various embodiments, the detection system 10 can be used to detect a trace amount of a gas in a short period time of a few seconds with few, if any, false positives or negatives.

The sampling system 22 can include, for example, an interferometer. The interferometer module can measure all optical frequencies produced by its source and transmitted through a sample (e.g., the sample 26 contained within the sampling system 22). An interference signal can be passed through the sample 26 and measured by the detector 30. The presence of different samples (e.g., a solid, liquid, or gas) can modulate the intensity of the radiation as detected by the detector 30. The output of the detector can be a variable, time-dependent. This output signal can be described as an interferogram. The interferogram can be represented as a plot of received energy intensity versus time (a "time domain" signal) (e.g., the interferogram can be a function of a variable optical path difference produced by a movable mirror's displacement). The interferogram can be understood to be a summation of all the wavelengths of energy emitted by the source and passed through the sample. Using the mathematical process of Fourier Transform (FT), a computer or processor can convert the interferogram into a spectrum that is characteristic of the light absorbed or transmitted through the sample. Because individual types of chemical compounds absorb specific wavelengths of energy, it is possible to determine the chemical compound(s) present in the sample based on the interferogram and the corresponding spectrum. In a similar manner, the magnitude of the energy absorbed by or transmitted through the sample can be used to determine the concentration of a chemical compound(s) in the sample.

In various embodiments, the source of the sample of gas 26 can be ambient air. The sampling system 22 (e.g., a gas sampling system) can collect surrounding air and introduce it to a sampling region of the sampling system 22. The sample of gas can be introduced to the sampling system 22 at a predetermined flow rate using a flow system including an inlet 46 and an outlet 50 of the sampling system 22.

In some examples, the detector 30 can be an infrared detector. In some embodiments, the detector 30 is a cooled detector. The processor 34 can receive signals from the detector 30 and identify a trace gas by its spectral fingerprint or provide a relative or absolute concentration for the particular material within the sample. The processor 34 can be, for example, signal processing hardware and quantitative analysis software that runs on a personal computer. The processor 34 can include a processing unit and/or memory. The processor 34 can continuously acquire and process spectra while computing the concentration of multiple gases within a sample. The processor 34 can transmit information, such as the identity of the trace gas, a spectrum of the trace gas, and/or the concentration of the trace gas, to a display 38. The processor 34 can save spectrum concentration time histories in graphical and tabular formats and measured spectrum and spectral residuals, and these can be displayed as well. The processor 34 can collect and save various other data for reprocessing or review at a later time. The display 38 can be a cathode ray tube display, light emitting diode (LED) display, flat screen display, or other suitable display known in the art.

Figure 2:
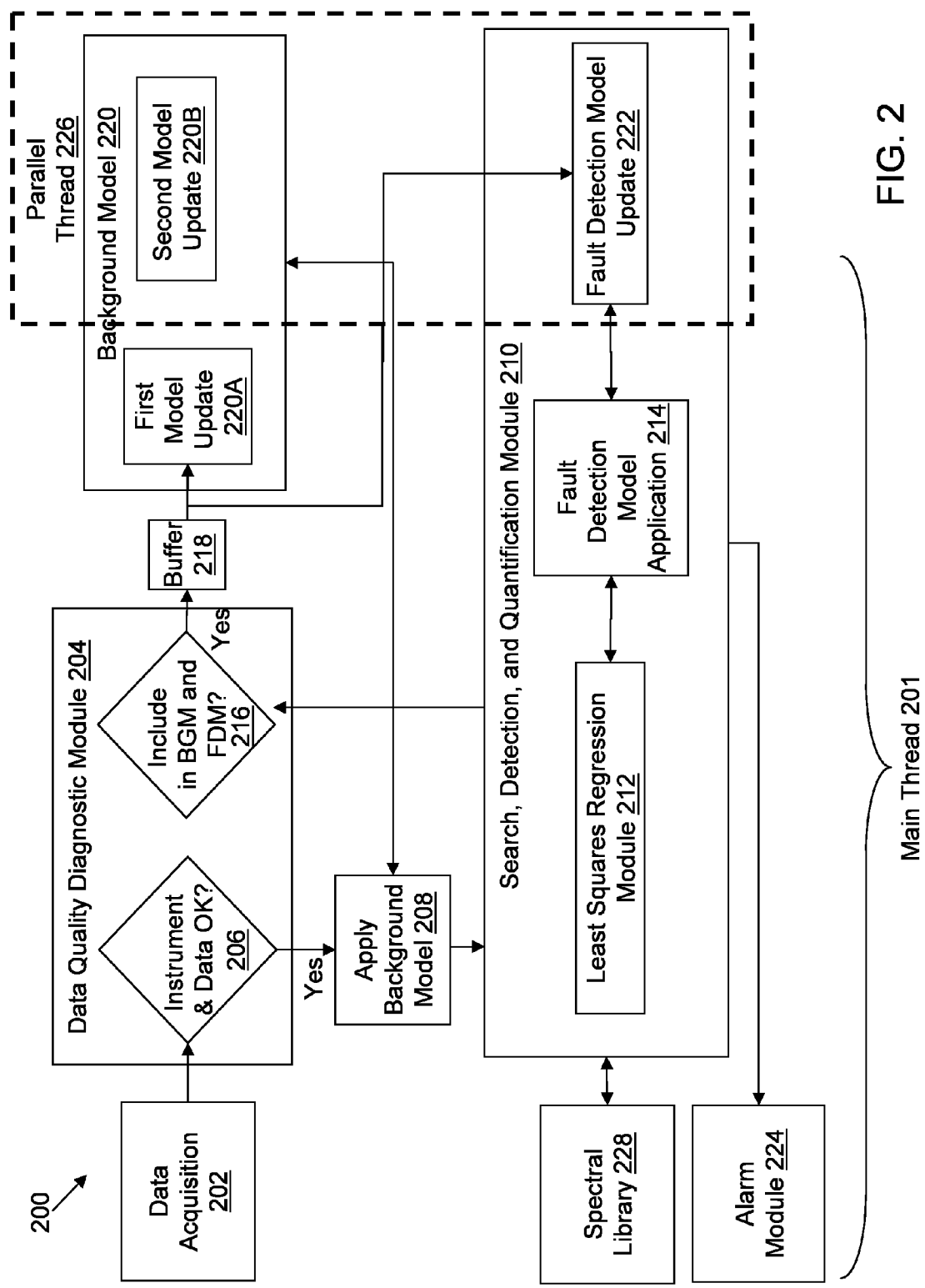
FIG. 2 illustrates an exemplary process flow for the detection system of FIG. 1 for monitoring and/or detecting and quantifying chemical compounds in a sample.

FIG. 2 illustrates an exemplary process flow 200 for the detection system 10 of FIG. 1 for monitoring, detecting, and/or quantifying chemical compounds in a sample. A sample (data) is acquired at 202 (e.g., via detector 30 of FIG. 1). At 206, the data quality diagnostic module 204 pre-processes the sample (e.g., to verify the integrity of the instrument and/or the sample). If the pre-processing does not successfully validate the sample and/or the instrument, then the data is discarded. If the pre-processing at step 206 successfully validates the sample, detection system 10 (via the processor 34) applies the background model at 208 to generate background corrected sample to remove any known background noise from the sample (see step 310 of FIG. 3). Advantageously the background corrected sample allows the detection system 10 to analyze the sample for unknown/unexpected chemicals and to ignore known/expected chemicals.

The search, detection, and quantification module 210 analyzes the background corrected sample to search for any primary chemicals (e.g., chemicals that are of a sufficient concentration that the detection system 10 triggers an alarm via alarm module 224). In some embodiments, the background model is not applied at 208, and the search, detection, and quantification module 210 processes uncorrected data. The search, detection, and quantification module 210 performs an iterative analysis of the background corrected sample to determine whether there are any primary chemicals (e.g., zero, one or up to "n" chemicals, where n can be predetermined by the detection system 10). The iterative analysis uses the least squares regression module is executed using the least squares regression module 212 and the fault detection model application module 214. These two modules are described in further detail below.

The search, detection, and quantification module 210 transmits the results of the primary chemical search to the data quality diagnostic module 204. At 216, the data quality diagnostic module 204 determines whether the sample should be incorporated into the background model (BGM) and/or the fault detection model (FDM). If the determination is yes, the data quality diagnostic module 204 transmits the sample to a time delay buffer 218. If the determination is no, then the data quality diagnostic module 204 discards the sample. For example, if the search, detection, and quantification module 210 identified zero primary chemicals, then the data quality diagnostic module 204 transmits the sample to the buffer 218 because updating the models (e.g., via the background model 220 and the fault detection model update 222) with the sample would not incorporate any primary chemicals into the sample. If, however, the search, detection, and quantification module 210 identified one or more primary chemicals, then the data quality diagnostic module 204 discards the sample and flush samples in the buffer 218 to prevent the primary chemicals from being incorporated into the background model (which could cause the detection system 10 to improperly ignore the primary chemicals).

The main thread 201 executes in real-time as the detection system 10 acquires data (e.g., on interferograms transmitted from the detector 30). The parallel thread 226 executes in the background (e.g., in non-real-time) to update the detection system 10 algorithms for detection, quantify and alarm of chemicals or gases of interest. The main thread 201 and the parallel thread 226 can execute as separate computer program threads, separate central processing unit (CPU) cores, separate computing systems, and/or the like. For example, the main thread 201 and the parallel thread 226 can be implemented as a multi-threaded architecture, where the main thread 201 is a first thread and the background thread 226 is a second thread.

Generally, the main thread 201 is configured to calculate the first model update (e.g., via the first model update module 220A), analyze real time spectroscopic measurements through the search, detection, and quantification module 210 comprising a fault detection model to identify one or more chemicals of interest (e.g., via the fault detection model application 214), and report the one or more chemicals of interest (e.g., via the alarm module 224). The main thread 201 outputs a set of processed absorbance spectra (e.g., background corrected absorbance spectra), background spectra (e.g., spectra to be used to update the background model), and a list of chemicals of interest and their associated concentrations detected and alarming information. This information can, for example, be streamed to the display 38 of FIG. 1 (e.g., a user interface) for real-time display and/or input to the buffer 218 such that the background model 220 and the fault detection model update 222 can retrieve the information to update the models.

Generally, the parallel thread 226 is configured to calculate the second model update (e.g., via the second model update module 220B) and to update the fault detection model (e.g., via the fault detection model update 222). Further, the parallel thread 226 can be configured to perform other functionality that can be run in parallel to the main thread 201. For example, the parallel thread 226 can execute some functionality described in the data quality diagnostic module, such as determining the performance of the detection system 10. In some examples, the parallel thread 226 can determine an update rate for the background model, the search, detection, and quantification algorithm, or both (e.g., via the data quality diagnostic module 204, based on an actual drift in instrument function, an environment condition, or both).

Referring to the data acquisition 202, the module can also acquire context data (e.g., timestamps, temperature, information about the detection system 10, signal levels (e.g., if the signal-to-noise dropped), etc.). The data acquisition module 202 operates on, for example, interferograms and/or diagnostic data for the detection system 10. Diagnostic data can include, for example, time, interferogram peak-to-peak (PP), interferogram direct current (DC), modulation efficiency, laser peak-to-peak (PP) (Volts (V)), laser direct current (DC) (V), the temperature of the detector (e.g., detector 30), laser frequency ($cm^{-1}$), flow rate of the sample gas (L/min), temperature of the cell (Celsius (C)) (e.g., within the sampling system 22, a gas cell, etc.), pressure (atm), pump (e.g., the pump that inputs the sample), temperature of incoming sample 26, temperatures of stirling detector 30 (Kelvin (K)), the temperature inside the detection system 10, the board temperature (e.g., the temperature of the circuit board components of the detection system 10 are implemented on), etc.

Referring to the data quality diagnostic module 204, the module determines whether to let data into the detection system (via 206) and whether to incorporate the data into the models (via 208). The data quality diagnostic module 204 can pre-process interferograms for use by other modules to generate a processed interferogram. For example, the pre-processing can include performing centerburst location alignment, scan direction alignment, scan direction correction, interferogram verification in its single length and magnitude, co-addition of two or more interferograms (e.g., averaging two or more sequential interferograms), high pass filter, and/or linearization. The data quality and diagnostic module 204 can be configured to process single sweep interferograms (10 interferograms/sec) and/or co-added interferograms, according to the application specification.

Referring further to the data quality and diagnostic module 204, the module can qualify the processed interferogram to generate absorbance spectra. For example, the data quality diagnostic module 204 qualifies the processed interferogram by detecting and logging the interferogram glitch and centerburst jump. The data quality diagnostic module 204 can tabulate the diagnostic data (e.g., the interferogram PP, interferogram DC, etc. as described above). The data quality diagnostic module 204 can transform the qualified interferogram, which is in the time domain, into the frequency domain. For example, the data quality diagnostic module 204 transforms the qualified interferogram into a transmittance spectrum. The transformation process into the frequency domain can include, for example, DC and slope correction, apodization, Fast Fourier Transforms (FFT), phase correction, and/or other transformations. The data quality diagnostic module 204 can use the transmittance to calculate absorbance spectra. The data quality diagnostic module 204 can transmit the absorbance spectra to the apply background model unit 208.

Referring further to the data quality diagnostic module 204, the module can store data and statistics that reflect the actual performance of the detection system 10 under the currently calibrated conditions. The data quality diagnostic module 204 can monitor the system performance (e.g., based on a system design specification). The data quality diagnostic module 204 can provide the detection limits for the target chemicals (e.g., the detection threshold for a chemical to be classified as a chemical of interest). The data quality diagnostic module 204 can calculate the detection distribution uncertainty, based on the algorithm executed by the search, detection, and quantification module 210, to estimate the detection limits.

Referring to the search, detection, and quantification module 210, the module detects whether there is a fault (e.g., via a fast executing process) and then performs a library search to fine tune the fault detection. Generally, the search, detection, and quantification module 210 first applies a mask function to the absorbance spectrum to generate a masked spectrum. A mask function (e.g., a weight function) can be, for example, an array of values (e.g., between 0 and 1) with the same dimension of the sample signal. A value of 0 excludes the corresponding variable completely from the signal, while 1 allows the variable to be processed normally. The higher the values are between 0 and 1, the greater the weight for the variable. The mask function can defined based on the absorbance peaks of common interferents (e.g., $H_2O$ and $CO_2$, two chemicals in air). The mask function can be predefined or determined dynamically. The mask function update can be implemented according to the quality and quantity of interferences (e.g. from spectral update module 130) by an EWMA algorithm. The search, detection, and quantification module 210 then executes a search, detection, and quantification algorithm on the obtained spectrum. The search, detection, and quantification module 210 generates concentration, spectral, residual, and t-values for any detected chemical compounds (or chemicals).

The fault detection model application 214 executes a first stage that identifies candidate chemicals. The first stage can include, for example, performing multivariate regression against the spectral library 228 (e.g., a library of chemical spectra) to calculate regression coefficients for each chemical in the library (e.g., using Equations 13-14 below). The first stage can include calculating a control chart based on the regression coefficients (e.g., using Equation 15). The first stage can include identifying top chemicals (the candidate chemicals) with the highest coefficients (e.g., the top "n" scores, where the number n is predetermined), which are passed to the second stage of the search, detection, and quantification module 210.

The least squares regression module 212 executes the second stage, which includes performing multivariate residual analysis on the top identified chemicals calculated by the fault detection model application 214. The second stage can include detecting (or identifying) the primary chemical with the highest residual reduction. For the detected chemical, the second stage (which is also referred to as "residual analysis") can include calculating a t-value (that measures the detection confidence) and/or a concentration of the chemical. The second stage can also include, for example, updating the residual spectrum based on the determined chemical. The updated residual spectrum (the spectrum with the primary chemical removed) can be fed back into the fault detection model application 214 for a next iteration of the first and second stages (e.g., if a candidate chemical is above a predetermined threshold). In each iteration, a single chemical (or chemical compound) can be identified until, for example, there are no sudden changes (e.g., no chemicals are identified with a highest residual reduction), and/or a maximum number of chemicals are determined. The search, detection, and quantification module 210 transmits data for the one or more chemicals of interest (e.g., the t-values and detected concentrations) to the alarm module 224. The data quality diagnostic module 204 can also buffer the data from the search, detection, and quantification module 210 in the buffer 218. Advantageously, the two stages in the search, detection, and quantification 210 allow the detection system 10 to quickly determine if a fault exists, and to then refine the data to determine the actual effect (e.g., whether to identify a primary chemical and to trigger an alarm).

Referring to the alarm module 224, this module makes a decision, based on the data associated with the one or more chemicals of interest, whether or not to trigger an alarm. If the alarm module 224 triggers an alarm, the module can also be configured to determine an alarm confidence level (e.g., low, medium, high). The alarm module 224 can define a separate alarm decision structure for each of the one or more chemicals of interest. For example, the alarm module 224 can determine whether the current concentration of a chemical of interest exceeds a user-defined threat concentration level (e.g., for chemical agents the threshold can be set to 0, for TICs, such as ammonia, the threshold can be set to many ppm). The alarm module 224 can use different alarm thresholds to calculate the alarm confidence level (e.g., the alarm module 224 can use low, medium and high confidence levels for low, medium, and high alarms, respectively). Various criteria (either alone or in combination) can be used to trigger an alarm. For example, a t-value can be preconfigured for an alarm, an "n and m" value can be set (e.g., if "n" out the last "m" spectra exceed the t-value, an alarm is triggered), and/or other alarm criteria can be configured. The alarm module 224 can also output an update flag indicative of the type of detection (e.g., which can be used to determine whether the current spectra should be used for an algorithm update). For example, the update flag can be an integer that is set to 0 if there was no chemical detection (e.g., including interferent and/or threat compounds), 1 if there was no threat detection (but there was an interferent detection), and 2 if there was no alarm (there was an interferent and/or threat compound detection but no alarm was triggered).

Referring to the background model 220, the first model update module 220A computes a first model of the background model 220 (e.g., by using Equation 4 as described below), based on the data in buffer 218. The data buffer 218 can prevent contamination resulting from slow chemical data poisoning the sample stream. For exemplary purposes only, assume samples are taken every tenth of a second, and that a chemical is slowly introduced into the sample such that the system can not detect the chemical for the first four minutes because the amount of the chemical is too small to cause it to be classified as a primary chemical (e.g., by the search, detection, and quantification algorithm). Further assume that at five minutes the level of the chemical is large enough to cause the system to classify the chemical as a primary chemical. If the background model is updated with each sample, the background model may slowly begin to incorporate the new chemical during the first four minutes when the system can not detect the chemical. This could cause the system to not detect the chemical after five minutes because the background model has incorporated the chemical. Advantageously, by setting the data buffer to a sufficient size (e.g., five minutes) to store data before incorporating it into the background model, the background model would not be updated to incorporate any of the measurements with trace amounts of the chemical. Once the system detects the chemical after four minutes, the data stored in the data buffer is discarded and not incorporated into the background model. In addition, the data quality diagnostic module 204 can be configured to allow the sample to be streamed into the buffer 218 based on one or more conditions. The conditions can be, for example, the sample did not cause any alarming, the sample did not include any detection of interest chemical(s), and/or the sample did not include any detection of interferent(s).

The size of the data buffer 218 can be calculated based on a delay time, such as two minutes (e.g., an amount of time the detection system 10 waits before updating the evolving background model). The data buffer 218 can be configured to continue updating when a background update flag is set to "ON." When the background update flag is set to "ON", the first model update module 220A retrieves the last sample (e.g., an interferogram) from the data buffer 218 and computes the first model into a spectrum (e.g., by using Equation 5 below). The first model update module 220A can flush the data buffer 218 when the background update flag is set to "OFF." The data buffer 218 will not fill again until the background update flag is set to the "ON" status. The second model can be calculated by the second model update module 220B. Advantageously, the first model update module 220A can update the first model of the background model 220, while the second model (or portions thereof) is calculated by the parallel thread 226.

The models used by the detection system 10 (e.g., the background model and the fault detection model) can be updated to factor in any instrument and/or environmental fluctuation (or drift). Advantageously, by buffering the evolving background data, the detection system 10 can prevent sample measurements (e.g., sample spectra) that are identified as having detected chemicals (e.g., interferent and/or targeted compounds) from being incorporated into the background model. Therefore, the spectra stored in the buffer 218 (and thus incorporated into the background model) can be considered "clean" spectra. The time delay applied to the data buffer can prevent the models from being contaminated by spectra which contain chemicals or gases of interest. For example, all spectra in the data buffer can be rejected when the detection system 10 detects chemicals or gases of interest from any spectrum in the buffer. Further, the detection system 10 can be configured, since the update of the algorithm models can involve time-consuming matrix operations, to update the models (e.g., by the parallel thread 226) independently from the analysis of chemical identification and quantification for individual sample (e.g., by the main thread 201).

Referring to the parallel thread 226, while the main thread 201 can be configured to execute in a high priority to assure that the detection system 10 analysis meets the desired processing speed, the parallel thread 226 can be configured to execute in background (e.g., with a relative low priority to update data in the buffer 218 as is necessary for the main thread 201). The spectral data used by the parallel thread 226 is updated by the data quality diagnostic module 204 as described above. The parallel thread 226 can receive data and results (e.g., from buffer 218).

Referring to the background model 220, the second model update module 220B calculates a second model for the background model 220 (e.g., a multivariate noise model as described below). The second model can be initialized by, for example, a pre-calibrated multivariate noise model or a few order polynomials. The second model update module 220B can calculate (or recalibrate) the second model (e.g., by using Equation 8 below). Advantageously, the second model can be updated to follow the drift of the instrument (e.g., the detection system 10 through laser PP and Laser DC) and/or the environment (e.g., ambient temperature and pressure).

For infrared spectroscopy, the infrared absorbance spectrum at time t (t=1, 2, . . . , τ), $a_t$, are linked to chemical concentrations by Beer's Law:

$$a_t = -\log(s_t / s_{t,0}) = l \sum_{i=0,1,\ldots}^{m} \varepsilon_i c_{i,t} + e_t \quad \text{Equation 1}$$

where:
$s_t$=the sample spectrum signal;
$s_{t,0}$=the background spectrum signal;
l=the path length over which the chemical is observed (e.g., this can be set as a constant for a given instrument);
$\varepsilon_i$=the absorption coefficients (as a constant array) for the chemical i (where i=1, 2, . . . , m chemicals in a chemical library);
$c_{i,t}$=the concentration at time t; and
$e_t$=the white noise term.

For Equation 1, $s_t$, $s_{t,0}$, and $\varepsilon_i$ are all functions of the light frequency, v (v=1, 2, . . . , n). Therefore, by measuring absorbance of a chemical (a species) at a known concentration, it is possible to determine the absorption of the chemical for the known concentration and a given wavelength (e.g., wavenumber). The absorption spectrum can be generated by measuring the absorbance of chemicals, at known concentrations, for a range of wavelengths. Equation 1 can be rewritten in matrix format:

$$A = -\log(S/S_0) = CK + E \qquad \text{Equation 2}$$

where:
A=an τ×n matrix of absorbance spectra;
S=the sample spectra;
$S_0$=the background spectra;
C=an τ×m concentration matrix;
K=an m×n constant matrix including path length and absorption coefficient information; and
E=an error matrix.

Figure 3:
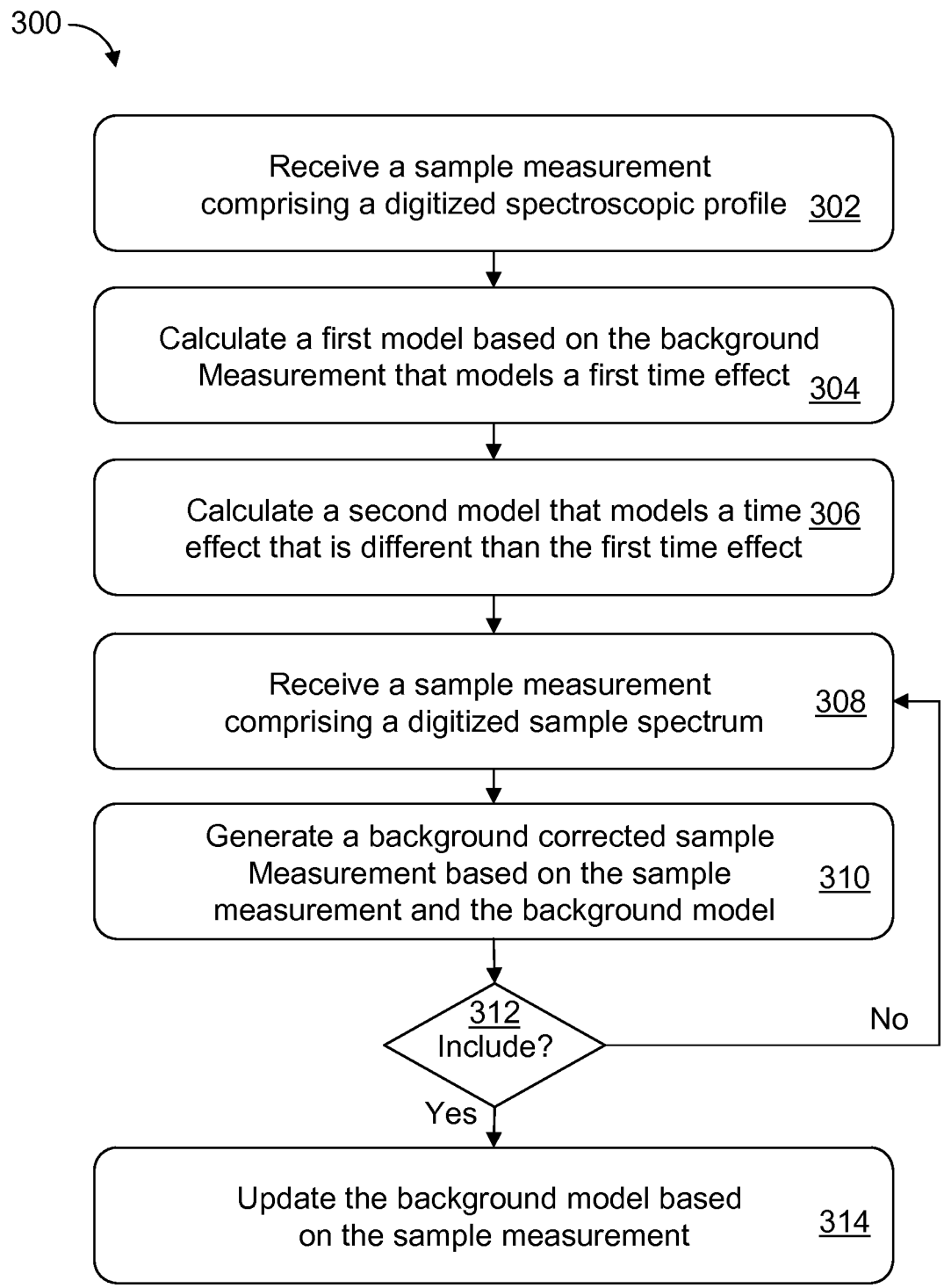
FIG. 3 illustrates an exemplary computer implemented method for generating a multivariate multistage background model.

A critical variable in Equation 2 is often $S_0$ (the "background spectrum" or "background spectra"), which is commonly approximated by a single background spectrum. However, in practice when using a single background spectrum, the systematic variation and spectral fluctuation can change over time such that the changes are non-negligible (e.g., as described with reference to FIG. 5). In some embodiments, the systems and methods described herein generate a background model to more accurately predict the background spectrum. FIG. 3 illustrates an exemplary computer implemented method 300 for generating a background model. While FIG. 3 depicts calculating a first and second background model in stages 304 and 306, the background model can include any number of stages. For example, the background model can include just stage 304 (e.g., an evolving background model), just stage 306 (e.g., a multivariate noise model), and/or any combination of stages 304 and/or stage 306 either alone or in combination with other stages (e.g., three stages, four stages, etc.).

At step 302, the detector 30 receives a background measurement (e.g., measured in a clean environment before a sample of interest is introduced) comprising a digitized spectroscopic profile. At steps 304 and 306, the background module calculates a background model using, for example, a background algorithm for a spectroscopic measurement process (e.g., via the first model update module 220A and the second model update module 220B, respectively). The background algorithm comprises calculating a first model based on the background measurement to model a first time effect (step 304, a first stage). For example, the background algorithm calculates an evolving background model based on the background measurement.

The background algorithm further comprises calculating a second model that models a time effect that is different than the first time effect (step 306, a second stage). The background algorithm can calculate the second model based on the sample measurement and/or the first model. For example, the background algorithm can calculate a multivariate noise model (e.g., $P'_{sys}$ from Equation 3) based on the background measurement and the first model. At step 308, the detector 30 receives a sample measurement (e.g., of the environment after the sample measurement was taken) that includes a digitized sample spectrum. At step 310, the processor 34 generates a background corrected sample measurement based on the sample measurement and the background model. At step 312, the background module determines whether the sample measurement is suitable for inclusion as an update to the multivariate multistage background model. If the background module determines it is suitable, method 300 proceeds to step 312. At step 312, the background module updates the background model based on the sample measurement. If the background model determines it is not suitable, method 300 proceeds back to step 308 and the process repeats.

The term "time effect" is used with respect to the first model and the second model to describe the difference between the models. For example, the first time effect is an averaged (e.g., long-term) model of the background drift and noise (e.g., an exponentially weighted moving average of the sample). The first model models a first time effect (e.g., an averaged or long-term effect) because when the curve of the first model is plotted against the curve of the actual background, the first model will closely approximate the background but will not perfectly match the background. The differences between the first model curve and the background curve are referred to as the residuals (e.g., the first model curve may be above or below the sample by an amount "delta" at a particular time period). The second model models the second time effect—the short-term residual profiles (e.g., the short-term differences between the first model and the actual background).

Generally, the detection system 10 measures one spectrum (e.g., the sample measurement) but uses the background corrected sample spectrum for detection (e.g., as described with reference to FIGS. 8-9). The detection system 10 can also average the sample measurement (e.g., if it does not include threat chemicals) into the existing first model (e.g., an evolving background model). For example, because an evolving background model may only describe the mean volume of spectrum, the evolving background model may not describe the difference between the actual system to a current measurement. This difference can be further modeled by the second model (e.g., a multivariate noise model). For example, a multivariate noise model can model noise residuals of the evolving background model.

Referring to steps 304-306, the background model can include and a digitized spectroscopic profile in a frequency domain (e.g., a spectrum generated by data quality diagnostic module 204). For example, the background model can include $S_0$ in equation 2. The digitized spectroscopic profile can be any type of spectrum. For example, the spectrum can be a spectroscopic spectrum (e.g., measured through FTIR) and/or a mass spectrum (e.g., measured through higher performance liquid chromatography (HPLC), liquid chromatography (LC), gas chromatography (GC)), and nuclear magnetic resonance (NMR).

Referring to step 304, the first model can be an evolving background model. The evolving background model can be updated frequently to correct any changes (e.g., significant changes) in the instrument and/or the environment that occur over time. Advantageously, the evolving background model allows infrared measurements to be calculated over a long period time (e.g., for analysis applications, such as a continuously monitoring point sensor). The term "evolving" is used with respect to the evolving background model to convey that the background model is changed in some way over time. For example, the signal-to-noise of the digitized spectroscopic profile can be averaged over an extended period of time. In some embodiments, the evolving background model is an averaged background model (e.g., a moving average background model or an un-weighted averaged background). The detection system 10 can generate the evolving background model by filtering background measurements with a low-pass filter to smooth the spectrum (e.g., in time series, such as filtering in one spectrum, e.g. 800 up to 4000). The evolving background model can be calculated and/or updated in either the time domain or the frequency domain, which is described further with respect to steps 402-404 of FIG. 4.

Referring to step 306, to more precisely model the background (e.g., to facilitate continuous analysis over a long period time), the second model models the remaining noise from the first model. For example, the background module can model and remove the noise from the first model using a multivariate noise model. The multivariate noise model can be, for example, an averaged multivariate noise model. Assuming the remaining noise of the first model can be described by a multivariate model, Equation 2 can be rewritten as:

$$A = CK + TP'_{sys} + E \qquad \text{Equation 3}$$

where:
A=an τ×n matrix of absorbance spectra;
C=an m×x concentration matrix;
K=an τ×m constant matrix;
T=an τ×$m_{sys}$ matrix of scores, obtained by projecting of the remaining spectra from the first model into the subspace $P_{sys}$;
$P_{sys}$=an n×$m_{sys}$ pre-defined multivariate subspace matrix that describes the remaining systematic noise of the first model (the transponation of $P_{sys}$ is indicated by a prime (')); and
E=an error matrix.

Referring to Equation 3, $m_{sys}$ is an integer constant. The value for $m_{sys}$ can be determined apriori (e.g., by a calibration dataset). The value can also be dynamically determined by a cross-validation approach based on a spectral matrix obtained in real-time. $P'_{sys}$, the multivariate noise model, can be solved for using Equation 3. The multivariate noise model can be defined using multivariate methods based on the absorbance spectra, diagnostic data, the first model, and other data. The multivariate methods can include, for example, Principal Components Analysis (PCA), Independent Components Analysis (ICA), Multivariate Curve Resolution (MCR), Partial Least Squares (PLS), Total Least Squares (TLS), Weighted Least Squares (WLS), Continuum Regression (CR), and Ridge Regression (RR). To implement the multivariate regression methods, the instrument and environment diagnostic data (e.g., time elapsed, ambient temperature, temperatures related to the system (e.g., to the detection system 10), sources (e.g., sample 26), the detector (e.g., the detector 30), related electronic circuitry, etc.) can be used as y-variables to regress against the remaining noise of the first model, the x-variable. The multivariate noise model can be updated as described with respect to steps 406-408 of FIG. 4.

Figure 4:
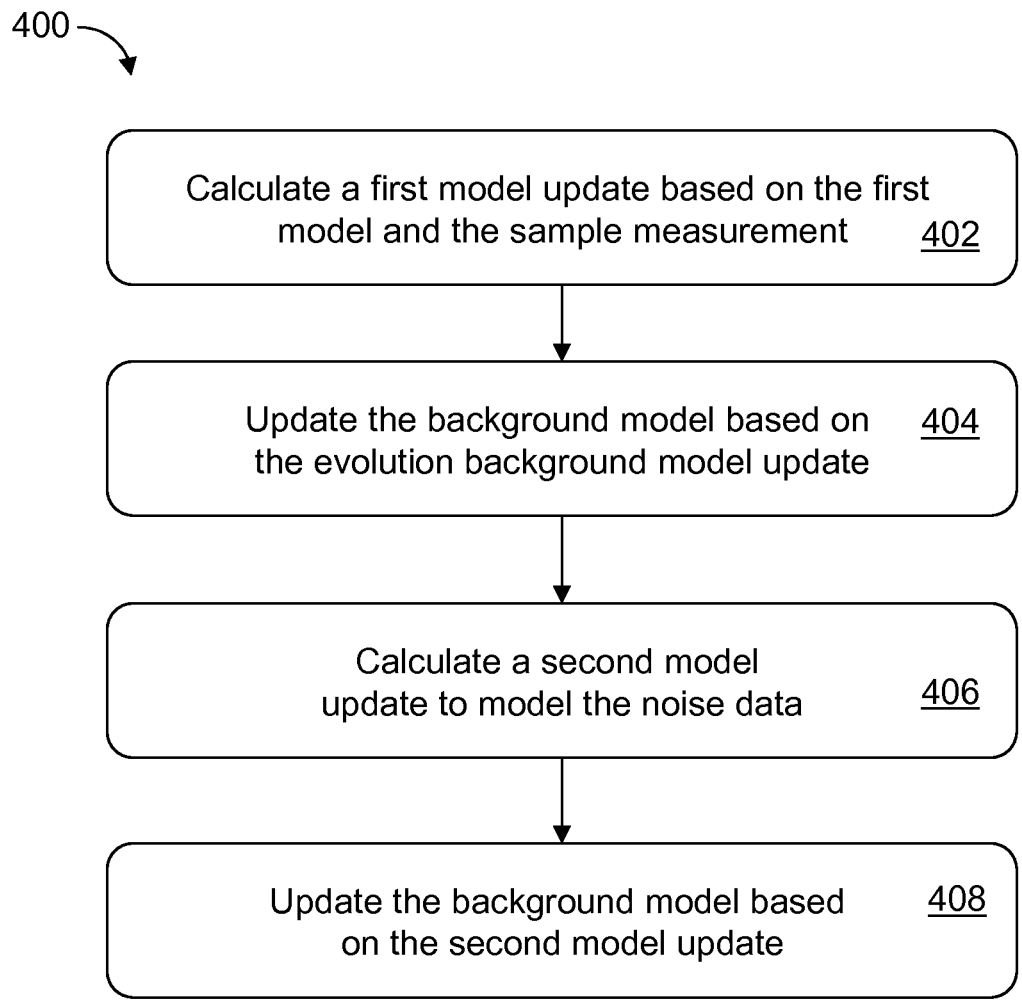
FIG. 4 illustrates an exemplary computer implemented method for updating a multivariate multistage background model.

FIG. 4 illustrates an exemplary computer implemented method 400 for updating a background model. At step 402, the first model update module 220A calculates a first model update based on the first model and the sample measurement, wherein the first model update comprises noise data (e.g., the noise data this is ultimately modeled and cancelled-out using the second model). At step 404, the first model update module 220A updates the background model based on the first model update. At step 406, the second model update module 220B calculates a second model update to model the noise data in the first model update. At step 408, the detection system 10 (e.g., via the second model update module 220B and/or the first model update module 220A) updates the background model based on the second model update, wherein the noise data from the first model update is reduced using the second model update.

Referring to steps 402-404, the first model update module 220A calculates a first model update. In some embodiments, the first model can be an exponentially weighted moving average (EWMA) model that is updated over time. The first model can be updated in either in time domain (e.g., based on a time domain update if the first model is an interferogram background), or frequency domain (e.g., based on a frequency domain update if the first model is a spectrum background). If, for example, the first model update module 220A maintains the first model in time domain, the update process can be described as:

$$i_{t+1,0} = \lambda_0 i_{t+1} + (1-\lambda_0) i_{t,0} \ (t=1, 2, \ldots, \tau) \qquad \text{Equation 4}$$

where:
t=time;
$i_{t+1,0}$=the time domain interferogram background update (e.g., the first model);
$i_{t+1}$=the next interferogram background at time t+1;
$i_{t,0}$=the mean historical interferogram background (e.g., the first model) at time t; and
$\lambda_0$=is an update constant that determines the speed of the background update, where $0 < \lambda_{0 \leq 1}$.

Referring to Equation 4, the first model update module 220A can calculate the first model based on an update constant or an update constant array. In some embodiments, $\lambda_0$ is an update constant, where the same value of $\lambda_0$ is used across the entire interferogram. For example, if an interferogram is used for the first model, the same constant (e.g., λ=0.9) is used for every point in the interferogram. A larger value of $\lambda_0$ can give more weight to the recent background observations and less weight to those that are further removed in time. A smaller value of $\lambda_0$ can give less weight to the recent background observations. In some embodiments, $\lambda_0$ can be an update constant array that provides various speeds for updating the variables of background in time domain. For example, an update constant of λ=0.9 is used for some interferogram points, an update constant of λ=0.8 is used for some interferogram points, an update constant of λ=0.1 is used for some interferogram points, etc. The constant array can be defined by a process that differentiates signals from noises.

The value(s) for $\lambda_0$ can be predetermined based on the system parameters (e.g., based on diagnostic data for the detection system 10 and/or information collected by data quality diagnostic module 204). The value(s) for $\lambda_0$ can be dynamically determined (or recalculated) to optimize, for example, the separation between spectral variation of interest and instrument/environment drift. For example, the first model update module 220A can vary $\lambda_0$ based on the drifting rate of the instrument, environment functions, or both (e.g., determined by the data quality diagnostic module 204). For example, if the environment is stable a value of λ=0.9 can be used, but if the environment becomes worse, then λ can be changed from 0.9 to 0.8 to reflect the change of the environment.

The first model update module 220A can maintain the first model in a frequency domain. If, for example, the first model (and update process) is maintained in the time domain as described above, the first model update module 220A can calculate the first model in the frequency domain. For example, the first model update module 220A can calculate the first model in the frequency domain using a Fast Fourier transform (FFT). The data quality diagnostic module 204 can apply the FFT after performing data processing of the background interferogram, including filtering, linearization, apodization function, phase correction, etc. The transformation can be described as:

$$s_{t+1,0} = \wp \, (i_{t+1,0}) \qquad \text{Equation 5}$$

where:
$s_{t+1,0}$=the background spectrum in frequency domain at time t+1;
$i_{t+1,0}$=the interferogram signal in time domain at time t+1; and
$\wp$ =the transformation operation process described above.

Advantageously, by using a first model (e.g., an evolving background model) that can be frequently updated, the systematic and spectral variation can be significantly reduced compared to using just a single background spectrum. The first model update module 220A can calculate a first model update (e.g., either $i_{t+1,0}$ in the time domain or $s_{t+1,0}$ in the frequency domain) based on the first model (e.g., based on $i_{t,0}$) and the sample measurement, wherein the first model update comprises noise data (e.g., the noise data this is ultimately modeled and cancelled-out using the second model). However, in some embodiments, using just the first model alone (e.g., just the first stage of the background model) may still not whiten all the noise. For example, the systematic change may not be negligible when using just the single background spectrum.

Referring to steps 406-408, the second model update module 220B calculates a second model update. The second model update module 220B can filter the second model based on the first model. The second model update module 220B can correct the remaining spectral variation of the multivariate noise model based on a multivariate approach. The detection apparatus 10 can frequently update the second model to reflect instrument and environment changes over time (e.g., both subtle and obvious changes). For example, the detection apparatus 10 can rotate the coordinate axles of the second model based on changes in new spectral data. The detection apparatus 10 can also evolve the second model over time (e.g., averaged, EWMA, etc.). For example, EWMA can be used in combination with the multivariate methods described above. In some embodiments, the second model update is calculated using an EWMA in a noise subspace expanded by the second model using Exponentially Weighted Moving—Principal Components Analysis (EWM-PCA), Exponentially Weighted Moving—Independent Components Analysis (EWM-ICA), Exponentially Weighted Moving—Multivariate Curve Resolution (EWM-MCR), Exponentially Weighted Moving—Partial Least Squares (EWM-PLS), Exponentially Weighted Moving—Total Least Squares (EWM-TLS), Exponentially Weighted Moving—Weighted Least Squares (EWM-WLS), Exponentially Weighted Moving—Continuum Regression (EWM-CR), and Exponentially Weighted Moving—Ridge Regression (EWM-RR). An exemplary description of EWM-PCA is provided below with Equations 6-12. Further detail on EWM-PCA can be found in S. Wold, *Exponentially weighted moving principal components analysis and projection to latent structures, EWMPCA and EWM-PLS*. Chemom. Intell. Lab. Syst. 23, p. 149-161 (1994), which is hereby incorporated by reference herein in its entirety. The EWM-PCA can include two calculation components. In the first part of the EWM-PCA algorithm, the second model update module 220B calculates the second model by calculating updated process values in a next time point based on the digitized spectroscopic profile (e.g., using Equation 6). In the second part, a PCA model for the drifting process is initiated and updated.

Referring to the first part of the EWM-PCA algorithm, process values are updated based on the current process values and forecasted in the next time points, t+1, according to:

$$\hat{t}_{t+1} = a_{t+1}\hat{P}_{t,sys} \quad \text{Equation 6}$$

where:
$\hat{t}_{t+1}$=an $1 \times m_{sys}$ vector representing the forecasted process values at t+1;
$a_{t+1}$=a sample spectrum at time point t+1; and
$\hat{P}_{t,sys}$=a subspace of the background noise model, defined by the loadings of the EWM-PCA model at time t.

The remaining color noise is estimated by Equation 6 and the final sample spectrum is calculated by:

$$\hat{a}_{t+1} = a_{t+1} - \hat{t}_{t+1}\hat{P}'_{t,sys} \quad \text{Equation 7}$$

where:
$\hat{a}_{t+1}$=the final sample spectrum, corrected by the evolving background model and the background noise model;
$a_{t+1}$=a sample spectrum at time point t+1, corrected by the evolving background model; and
$\hat{P}'_{t,sys}$=the transportation of $\hat{P}_{t,sys}$.

Referring to the second part of the EWM-PCA algorithm, the second model update module 220B (a) initiates (or calculates) the initial second model and (b) updates the second model (e.g., to reflect the instrument and environment fluctuation). Regarding initialization, after the first model is calculated as described above, the sample spectra $A_t$ is decomposed:

$$A_t = T\hat{P}'_{t,sys} + E(t=cal) \quad \text{Equation 8}$$

where:
$A_t$=an $\tau(cal) \times n$ matrix of sample spectra, where $\tau(cal)$ is the number of sample spectra used to calibrate the model (e.g., to build the second model);
T=an $\tau(cal) \times m_{sys}$ matrix of scores;
$\hat{P}'_{t,sys}$=loadings of the initial second model; and
E=an error matrix.

The initial second model, $\hat{P}'_{t,sys}$, can be calculated using PCA, ICA, MCR, PLS, TLS, WLS, CR, and RR as described above with reference to step 306 of FIG. 3. The second model update module 220B can update the second model when a new matrix $\tau(cal+1) \times n$ of sample spectra is ready to use (e.g., is ready in the buffer 218). The second model update module 220B can update the second model by rotating the axes of the $\hat{P}'_{t,sys}$ subspace established in the initiation step (e.g., Equation 8) according to Equations 9, 10 and 11 below to minimize the residual profile that is defined by Equation 12:

$$T_{t+1} = A_{t+1}\hat{P}_{t,sys} \quad \text{Equation 9}$$

where:
$T_{t+1}$=Scores at time t+1, estimated by projecting the sample spectra at time t+1 into the subspace of background noise model defined at time t;
$A_{t+1}$=the sample spectra at time t+1; and
$\hat{P}_{t,sys}$=the loadings of background noise model, defined at time t.

$$P_{t+1,sys} = A'_{t+1}T_{t+1}(T'_{t+1}T_{t+1})^{-1} \quad \text{Equation 10}$$

where:
$P_{t+1,sys}$=loadings at time t+1;
$A'_{t+1}$=the transportation of the sample spectra at time t+1;
$T_{t+1}$=an $\tau \times m_{sys}$ matrix of scores at time t+1; and
$T'_{t+1}$=the transponation of an $\tau \times m_{sys}$ matrix of scores at time t+1.

$$\hat{P}_{t+1,sys} = \lambda_{sys}\hat{\lambda}_{sys}P_{t+1,sys} + (1-\lambda_{sys})\hat{P}_{t,sys} \quad \text{Equation 11}$$

where:
$\hat{P}_{t+1,sys}$=the second model update at time t+1;
$\lambda_{sys}$=a constant, $0 < \lambda_{sys} \leq 1$, that determines the speed of rotation for the second model;
$P_{t+1,sys}$=Same from Equation 10; and
$\hat{P}_{t,sys}$=Same from Equation 9.

$$\min_{\hat{p}_{t+1,v,sys}} \left[ \sum_{v=1,2,...}^{n} \sum_{t=1,2,...}^{\tau} (a_{t+1,v} - t_{t+1}\hat{p}_{t+1,v,sys})^2 / n\tau \right] \quad \text{Equation 12}$$

where:

$t_{t+1}$=an element of matrix $T_{t+1}$;
$\hat{p}_{t+1,v,sys}$=an element of matrix $\hat{P}_{t+1,sys}$;
n=the number of variables in a sample spectrum; and
τ=the number of sample spectra at time t+1.

Referring to Equation 11, $\hat{P}_{t+1,sys}$ (the second model update) models noise data associated with the first model. $\hat{P}_{t,sys}$ was calculated using multivariate techniques; Equation 11 allows new data to be incorporated into the second model. $\hat{P}_{t+1,sys}$ is calculated based on the residual profile for the initial second model using Equation 12, and by rotating the axes of the initial second model $\hat{P}'_{t,sys}$ to minimize the residual profile. The residual profile is calculated using Equations 9-11. Referring to Equation 11, the same value of $\lambda_{sys}$ can be used for the entire EWM-PCA process, or $\lambda_{sys}$ can be calculated based on the system specification (e.g., diagnostic data) and/or performance monitor data calculated by the data quality diagnostic module 204. The dimensions of the $\hat{P}'_{t,sys}$ subspace can be configured to be constant or determined on the fly. Advantageously, using the background model (e.g., the first model and/or the second model) can significantly reduce the spectral variation.

Figure 5:
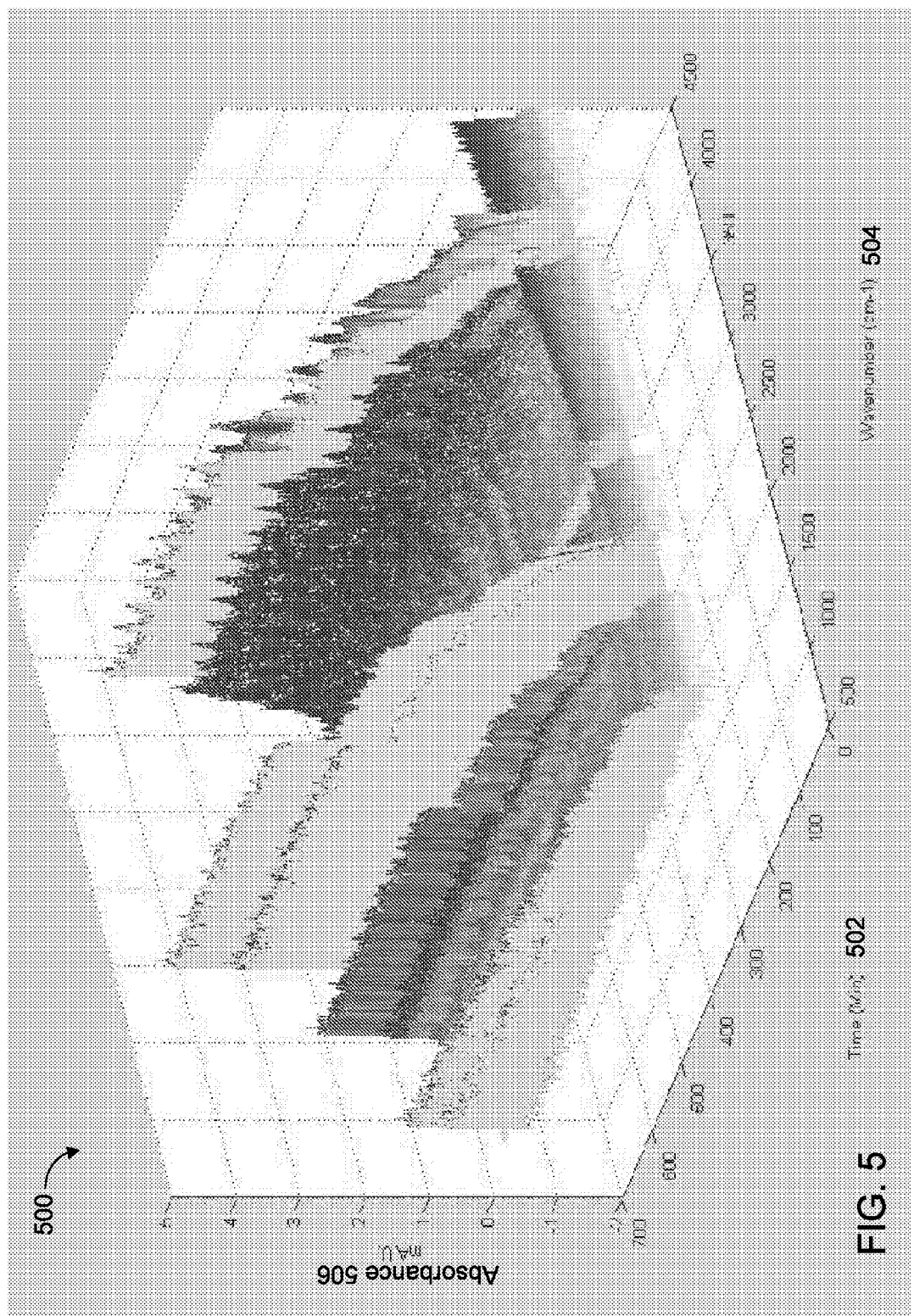
FIG. 5 illustrates an exemplary graph of sample spectra measured using a single background spectrum.

FIG. 5 illustrates an exemplary graph 500 of sample spectra measured using a single background spectrum (or interferogram). The time axis 502 is represented in minutes (min), spanning zero to seven hundred min. The wavenumber axis 504 is represented in inverse centimeters ($cm^{-1}$), spanning from 500 to 4500 $cm^{-1}$. The absorbance axis 506 is represented in milli-Absorbance Units (mA.U.), spanning from −2 to 5. The single background spectrum was calculated prior to taking measurements, and was not updated over time. After calculating the background spectrum, the detection system measured ambient air for ten hours. For the ambient air, the only chemical changes are $H_2O$ and $CO_2$. However, graph 500 shows that over ten hours, in addition to the spectral fluctuation due to the two gases, symmetrical variation was also observed (e.g., the fluctuations at 1000, 1500, 2000 and between 3500-4000 $cm^{-1}$. Even in the first few hours (e.g., between times 0 and 120), the fluctuation became non-negligible. As time progressed (e.g., between 400 and 700 min), the spectral variation was over 4 mA.U.

Figure 6:
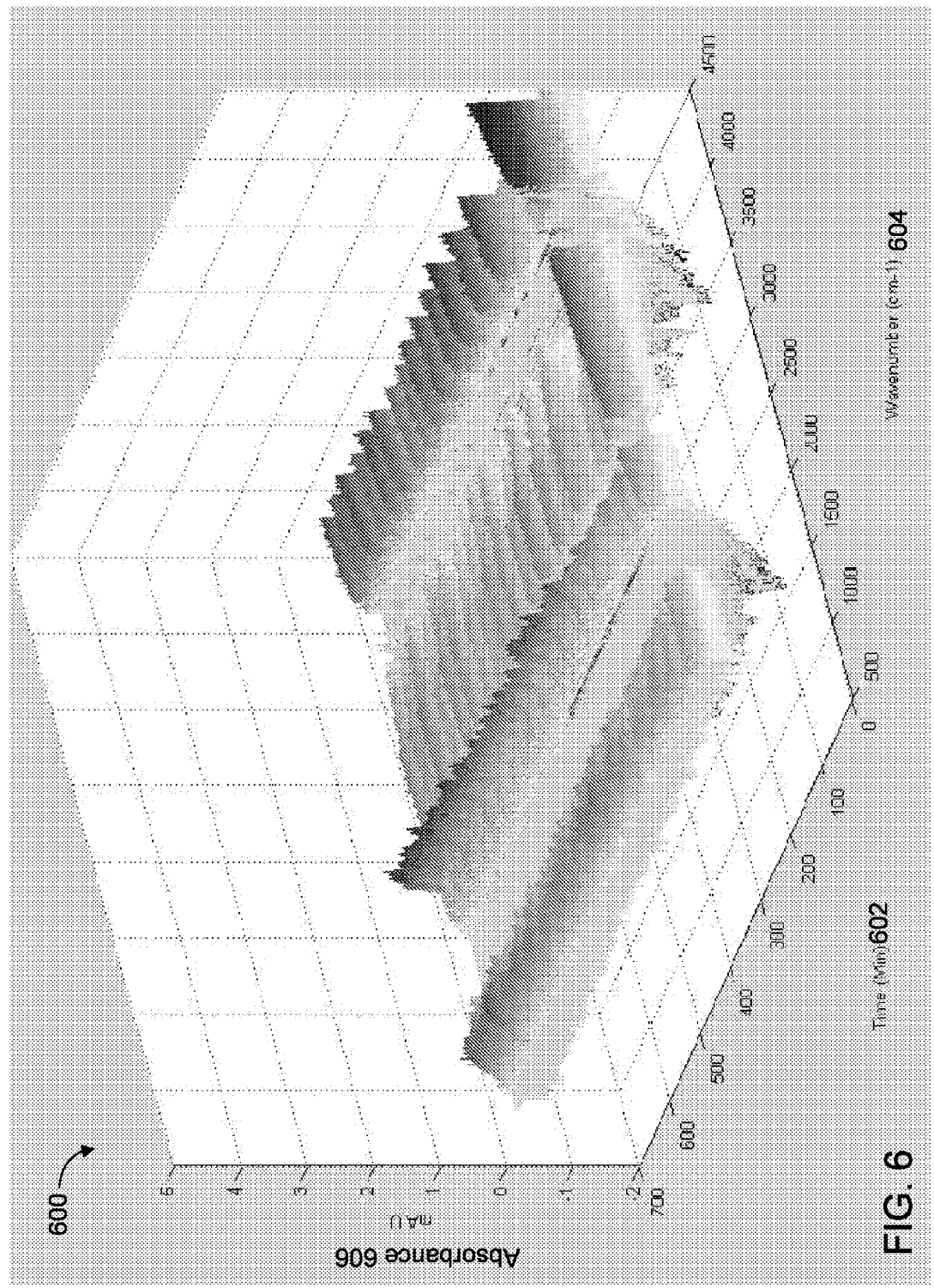
FIG. 6 illustrates an exemplary graph of sample spectra measured using an evolving background model.

FIG. 6 illustrates an exemplary graph 600 of sample spectra measured using a first model. The time axis 602 is represented in minutes (min), spanning zero to seven hundred min. The wavenumber axis 604 is represented in inverse centimeters ($cm^{-1}$), spanning from 500 to 4500 $c^{-1}$. The absorbance axis 606 is represented in milli-Absorbance Units (mA.U.), spanning from −2 to 5. The first model (e.g., an EWMA background model) was calculated prior to taking measurements (e.g., as described in step 304 of FIG. 3). After calculating the background spectrum, the detection system measured ambient air for ten hours. The first model was updated over time as the detection system measured the ambient air (e.g., as described in steps 402-404 of FIG. 4). As with FIG. 5, the only chemical changes for ambient air are $H_2O$ and $CO_2$. Graph 600 shows that over the full ten hour period, the spectral variation was below 1 mA.U. Advantageously, using the first model in place of the single background spectrum greatly reduced the spectral variation over time. However, the remaining is still not white noise (e.g., a spectral variation of less than 0.1 mA.U.

Figure 7:
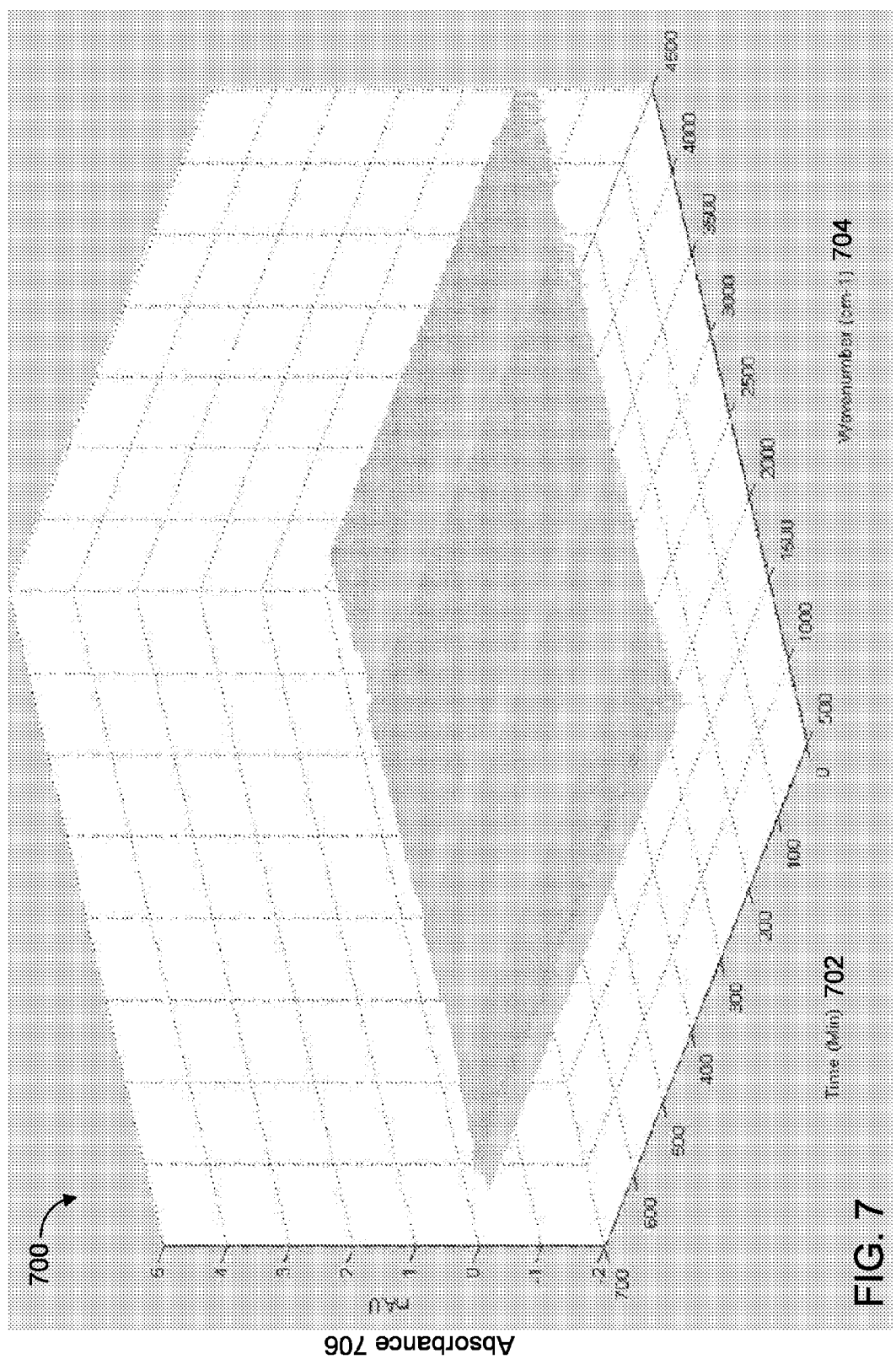
FIG. 7 illustrates an exemplary graph of sample spectra measured using a multivariate multistage background model.

FIG. 7 illustrates an exemplary graph 700 of sample spectra measured using a background model. The time axis 702 is represented in minutes (min), spanning zero to seven hundred min. The wavenumber axis 704 is represented in inverse centimeters ($cm^{-1}$), spanning from 500 to 4500 $cm^{-1}$. The absorbance axis 706 is represented in milli-Absorbance Units (mA.U.), spanning from −2 to 5. The background model (e.g., including a first model and a second model, such as an EWMA background model and an EWM-PCA background model) was calculated prior to taking measurements (e.g., as described in steps 304 and 306 of FIG. 3). After calculating the background model, the detection system measured ambient air for ten hours. The background model was updated over time as the detection system measured the ambient air (e.g., as described in FIG. 4). As with FIGS. 5 and 6, the only chemical changes for ambient air are $H_2O$ and $CO_2$. Graph 700 shows that over the full ten hour period, the spectral variation was still further reduced than using just the first model (as shown in FIG. 6). While approximately 70% of the total spectral variation was removed by the evolving background, approximately an additional 27% of the spectral variation was removed by using the second model (such that the final spectral variation is less than 3%). The reduced spectral variation decreases the detection limit (which increases the sensitivity of the detection system). For example, the average detection limit when using just a first model ranges between 10-15 parts-per-billion (ppb), whereas the average detection limit when using the background model (e.g., also using the second model) ranges between 1-5 ppb.

Figure 8:
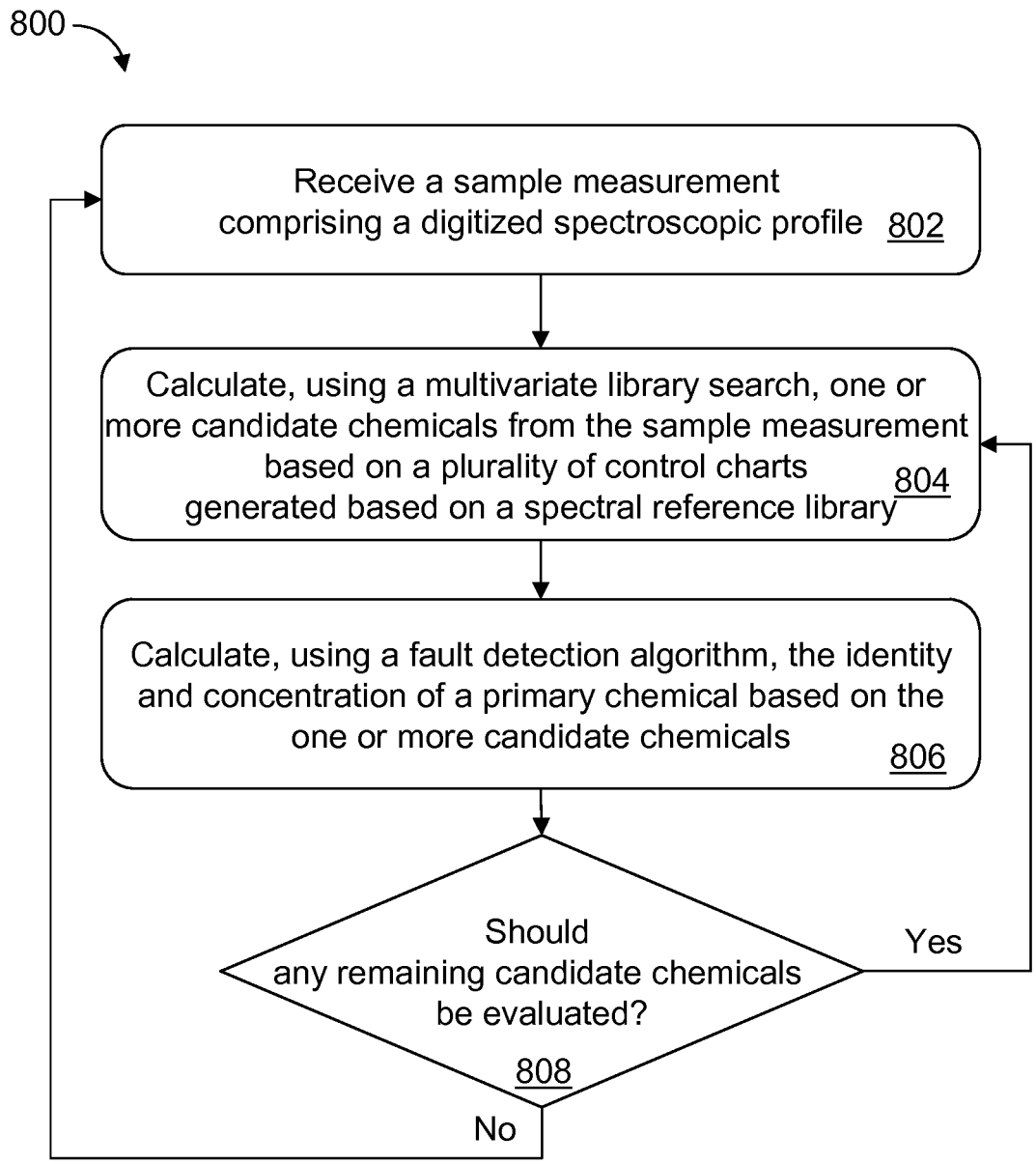
FIG. 8 illustrates an exemplary computer implemented method for monitoring, detecting and quantification of chemical compounds in a sample using a multivariate multistage library search, fault detection, and quantification algorithm.
Figure 9:
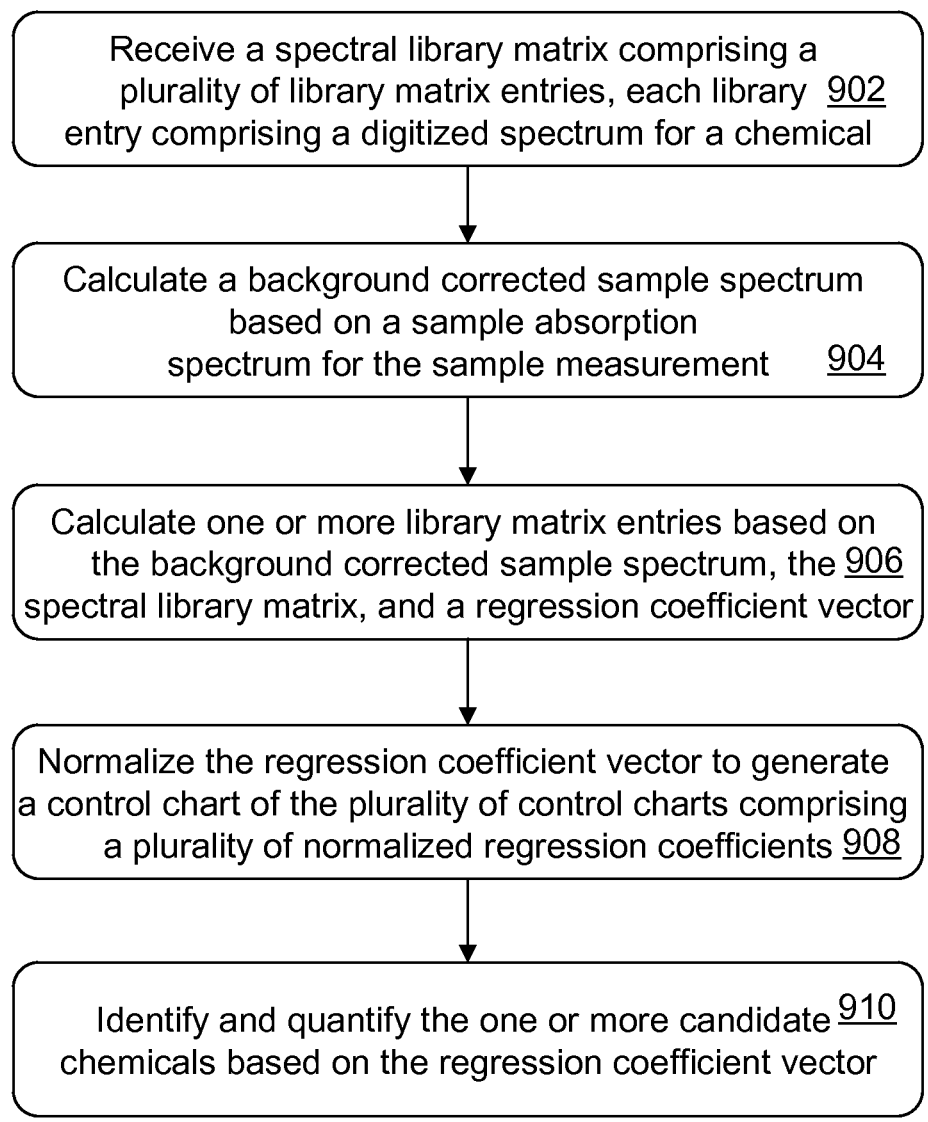
FIG. 9 illustrates an exemplary computer implemented method for identifying one or more candidate chemicals in a sample.

FIG. 8 illustrates an exemplary computer implemented method 800 for detecting and monitoring chemical compounds in a sample using a search, detection, and quantification algorithm. At step 802, the processor 34 receives a sample measurement comprising a digitized spectroscopic profile (e.g., from the detector 30). The search, detection, and quantification algorithm can be repeatedly executed each time the system receives a sample measurement. The search, detection, and quantification module 210 calculates one or more primary chemicals for the sample measurement using a search, detection, and quantification algorithm for analyzing and interpreting real time spectroscopic measurements. Specifically, the search, detection, and quantification module 210 calculates, using a multivariate library search, one or more candidate chemicals from the sample measurement based on a plurality of control charts generated based on a spectral reference library (step 804, the library search stage executed by the least squares regression module 212 of FIG. 2). The search, detection, and quantification module 210 calculates, using a fault detection algorithm, a primary chemical based on the one or more candidate chemicals (step 806, the fault detection stage executed by the fault detection model application 214 of FIG. 2). While FIG. 8 depicts two stages in the search, detection, and quantification algorithm, the search, detection, and quantification algorithm can include any number of stages (e.g., just step 804, just step 806, or steps 804 and 806 in combination with one or more additional stages).

At step 808, the search, detection, and quantification module 210 determines whether any of the remaining candidate chemicals (e.g., of the candidate chemicals with the exclusion of the candidate chemical determined to be a primary chemical) should be evaluated again by the search, detection, and quantification module 210. For example, the search, detection, and quantification module 210 can determine that one or more of the remaining candidate chemicals are above a predetermined threshold, and therefore should be further evaluated to determine if there are any remaining primary chemicals. If step 808 determines one or more of the remaining candidate chemicals should be evaluated, the method 800 proceeds to step 804. Otherwise the method 800 proceeds back to step 802 to evaluate the next sample measurement.

Referring to step 802, the sample measurement can be a background corrected sample measurement calculated based the background model (e.g., calculated as described above in step 310 of FIG. 3). Referring to step 804, this step is the first stage of the search, detection, and quantification algorithm: the library search stage. The search, detection, and quantification module 210 can execute a multivariate library search (e.g., against a spectral library 228 of known chemicals) using regression (e.g., PLS). The search, detection, and quantification module 210 can, based on the regression, build control charts for each chemical in the spectral library (e.g., if there are 365 chemicals library, the search, detection, and quantification module 210 builds 365 control charts). Advantageously, the fault detection stage generates a list of candidate chemicals that are highly recommended for further processing by the second stage.

Further referring to step 804, the one or more candidate chemicals can be identified based on a matrix-based simultaneous comparison comprising a least squares regression. The least squares regression can include, for example, partial least squares or inverse least squares. FIG. 9 illustrates an exemplary computer implemented method 900 for identifying one or more candidate chemicals in a sample during the library search stage of the search, detection, and quantification algorithm. At step 902, the search, detection, and quantification module 210 receives the spectral reference library (e.g., $K_{Library}$ of Equation 13). At step 904, the search, detection, and quantification module 210 calculates a background corrected sample spectrum (e.g., $\hat{a}_{t+1}$ of Equation 13 below) based on a sample absorption spectrum (e.g., $a_{t+1}$ of Equation 14 below) for the sample measurement. At step 906, the search, detection, and quantification module 210 calculates one or more library matrix entries. The search, detection, and quantification module 210 calculates the library matrix entries based on the background corrected sample spectrum, the spectral reference library, and a regression coefficient vector (e.g., using Equations 13 and 14]). At step 908, the search, detection, and quantification module 210 normalizes the regression coefficient vector to generate a control chart (e.g., $b'_{t+1}$ of equation 15 below) that includes a plurality of normalized regression coefficients. At step 910, the search, detection, and quantification module 210 identifies and quantifies the one or more candidate chemicals based on the regression coefficient vector. Each of the one or more candidate chemicals is associated with a corresponding normalized regression coefficient that is larger than a predetermined control threshold (e.g., determined using Equations 15 and 16 below).

Referring to step 902, the search, detection, and quantification module 210 receives the spectral reference library $K_{Library}$, an $k_{Library} \times n$ matrix, which includes sample chemical absorbencies. For example, if $K_{Library}$ includes 366 library matrix entries, $k_{Library}=365$. Each library matrix entry includes data for a sample (or model spectrum for a chemical). For example, each library matrix entry can include absorbance data for a chemical over a range of wavenumbers (e.g., absorbance data for wavenumbers 800-1200 cm$^{-1}$, and therfore n=400). The spectral reference library can be constant. In some examples, the spectral reference library can be updated to include or exclude spectra. For example, the spectral reference library can be dynamically updated to include or exclude spectra.

Referring to step 904, the search, detection, and quantification module 210 calculates a background corrected sample spectrum based on a sample absorption spectrum. The multivariate library search algorithm is applied to the background corrected sample spectrum at time t+1:

$$\hat{a}_{t+1} = b_{t+1} K_{Library} \quad \text{Equation 13}$$

where:

$\hat{a}_{t+1}$=the multivariate multistage background corrected sample spectrum at time t+1;

$b_{t+1}$=a regression coefficient vector (with dimensions $1 \times k_{Library}$) at time t+1; and $K_{Library}$=the spectral reference library.

Advantageously, by using the spectral reference library, the system can achieve a fast implementation time to identify the candidate chemicals. To increase the robustness of the library search, the linear regression shown in Equation 13 can be directly applied to the absorbance spectrum:

$$a_{t+1} = b_{t+1}[(K_{Library} \hat{P}_{t,sys})] \quad \text{Equation 14}$$

where:

$a_{t+1}$=the sample absorbance spectrum (e.g., a sample spectrum corrected by the evolving background model $\hat{a}_{t+1}$ is further corrected based on $a_{t+1}$);

$b_{t+1}$=a regression coefficient vector (with dimensions $k_{Library}+k_{t,sys}$) at time t+1;

$K_{Library}$=the spectral reference library; and $\hat{P}_{t,sys}$=the second model (e.g., calculated in real-time as described with reference to step 304 of FIG. 3 and steps 406-408 of FIG. 4).

Referring to Equation 14, the search, detection, and quantification module 210 augments $K_{Library}$ with $\hat{P}_{t,sys}$, the second model, to generate an augmented spectral reference library. For example, assume there are 365 chemicals in the spectral reference library, where each chemical includes a chemical spectrum with 1,000 variables (so $K_{Library}$ is $k_{Library}$=365 by n=1000). The search, detection, and quantification module 210 augments (or adds) the second model into the spectral reference library. For example, if the second model comprises three vectors, then the second model is augmented to $K_{Library}$ to achieve dimensions of ($k_{Library}+k_{t,sys}$)=368 by n=1000. The search, detection, and quantification module 210 linearly regresses the sample absorption spectrum, $a_{t+1}$, based on the augmented spectral reference library. The linear regression can be implemented using regression methods such as, for example, PLS, PCR, GLS, CLS, WLS, CR, etc.

Referring to step 908, a control chart is built for each spectral library entry. The search, detection, and quantification module 210 can normalize regression coefficient vector:

$$b'_{t+1} = b_{t+1}/\hat{\delta}_{b(cal),t+1} \quad \text{Equation 15}$$

where:

$b'_{t+1}$=the normalized regression coefficient vector to build the control chart;

$b_{t+1}$=the regression coefficient vector (with dimensions $k_{Library}+k_{t,sys}$) at time t+1; and $\hat{\delta}_{b(cal),t+1}$=a $1 \times (k_{Library}+k_{t,sys})$ vector of the normalization factors for the control chart of time t+1, which is updated over time through Equations 16 by using an exponentially weighted moving average update, described as:

$$\hat{\delta}_{b(cal),t+1} = \lambda_{Library} \hat{\delta}_{b(cal),t+1} + (1-\lambda_{Library})\delta_{b(cal),t} \quad \text{Equation 16}$$

where:

$\lambda_{Library}$=the update constant; and $\hat{\delta}_{b(cal),t}$=the normalization factors for control chart of time t; and $\delta_{b(cal),t+1} = 1 \times (k_{Library} + k_{t,sys})$ vector of standard deviations for updating normalization factors at time t+1, which is calculated according to Equation 17 as below:

$$\delta_{b(cal),t+1} = \sqrt{\frac{\sum_{t=t+1,\ldots,t+1+\tau(cal)} \left[ b_{t+1(cal)} - \sum_{t=t+1,\ldots,t+1+\tau(cal)} b_{t+1(cal)}/\tau(cal) \right]^2}{\tau(cal)-1}}$$

Equation 17 where:
$b_{t+1}(cal) = $ a $1 \times (k_{Library} + k_{t,sys})$ vector of regression coefficients of sample spectra in a calibration dataset at time t+1; and
$\tau(cal) = $ number of sample spectra in the calibration data set.

Referring to Equation 16, the update constant $\lambda_{Library}$ can be calculated based on instrument drift and/or environment drift. If the search, detection, and quantification module 210 determines that any value from the normalized regression coefficients, $b'_{t+1}$, is larger than a predetermined control threshold, the search, detection, and quantification module 210 identifies the associated chemical as a candidate chemical (e.g., identifies the chemical as having a sudden change). The candidate chemicals are used by the second stage to determine whether the sudden change is due to the instrument and/or environment fluctuation or due to other reasons (e.g., due to a chemical release).

Referring to step 806, this step is the second stage of the search, detection, and quantification algorithm: the fault detection stage. The search, detection, and quantification module 210 confirms the calculations performed by the first stage. For example, the search, detection, and quantification module 210 determines whether a candidate chemical from the one or more candidate chemicals should be identified as a primary chemical. In some examples, the search, detection, and quantification module 210 may determine that none of the one or more candidate chemicals should be identified as a primary chemical. This can occur, for example, on the first execution of method 800 on the sample measurement, or on a subsequent iteration of method 800 if the search, detection, and quantification module 210 determines the remaining candidate chemicals should be evaluated (step 808).

Referring to step 808, the search, detection, and quantification module 210 can calculate a residual that is used in step 804 has the most recently determined primary chemical removed from the data. For example, the search, detection, and quantification module 210 can calculate a residual profile by subtracting the identified primary chemical from the sample measurement. At step 804, the search, detection, and quantification 210 identifies a second set of one or more candidate chemicals in the residual profile based on a comparison of the residual profile to the spectral reference library. At step 806, the search, detection, and quantification module 210 identifies a second primary chemical based on a focused chemical evaluation of the second set of one or more candidate chemicals (or determines that none of the candidate chemicals in the second set are primary chemicals). Upon completion of the method 800, the listing of primary chemicals can be reported (e.g., to a user, to a database, etc. to keep track of the chemicals of interest in the sample).

The search, detection, and quantification module 210 can use various metrics to gauge each candidate chemical. For example, the search, detection, and quantification module 210 can use a score, such as a $T^2$ residual reduction, a t-statistic (e.g., the first stage can also use a score, but the first stage can be configured as a preliminary library search to speed up the first stage). The search, detection, and quantification module 210 can be configured to select a certain number of primary chemicals. For example, the search, detection, and quantification module 210 can be configured to identify the highest five chemicals from the candidate chemicals (e.g., the five chemicals with the highest regression coefficients). For example, if the first stage provides ten candidate chemicals, the second stage can identify up to five primary chemicals from the ten candidate chemicals. As another example, if only four candidate chemicals are identified in the first stage, the second stage can only return a maximum of four primary chemicals.

Referring back to Equation 3, the candidate chemicals identified by the first stage are further analyzed using a residual analysis:

$$a_{t+1} = c_{t+1,Threat} K_{Threat} + c_{t+1,Interferent} \hat{K}_{Interferents,t+1} + t_{t+1} \hat{P}_{sys,t+1} + e_{t+1}$$

Equation 18 where:
$a_{t+1}$ = the sample spectrum at time t+1, corrected by the current evolution background model;
$c_{t+1,Threat}$ = threat concentrations at time t+1;
$K_{Threat}$ = a matrix that includes the spectra of known chemical threats;
$c_{t+1,Interferent}$ = interferent concentrations at time t+1;
$\hat{K}_{Interferents,t+1}$ = a matrix that includes the spectra of known chemical interferences, updated at time t+1;
$t_{t+1}$ = scores of the background noise model;
$\hat{P}_{sys,t+1}$ the second model at time t+1; and
$e_{t+1}$ = the spectral error at time t+1.

Referring to Equation 18, the equation is formatted to include four terms: the threat chemical term ($c_{t+1,Threat} K_{Threat}$), the interferent term ($c_{t+1,Interferent} \hat{K}_{Interferents,t+1}$), the color noise ($t_{t+1} \hat{P}_{sys,t+1}$) and white noise term ($e_{t+1}$). Mathematically, Equation 18 can be described below according to Equation 19, similar to Equations 1 and 2:

$$a_{t+1} = c_{t+1} K + e_{t+1}$$

Equation 19 where:
$a_{t+1}$ = the term in Equation 18;

$c_{t+1} = [c_{t+1,Threat}\ c_{t+1,Interferent}\ t_{t+1}]$; and $K = [K'_{Threat}\ K'_{Interferents}\ P'_{sys}]'$.

Various regression methods can be used to calculate the residual analysis (e.g., PLS and the other regression methods previously mentioned). Equations 18 and 19 can be generalized to simplify the mathematical calculations:

$$\hat{c}_{t+1} = a_{t+1} \hat{K}_{t+1}^+$$

Equation 20 where:
$\hat{c}_{t+1}$ = the estimated parameter vector;
$a_{t+1}$ = the sample spectrum, same as in previous two equations;
$\hat{K}_{t+1}^+$ = the combined matrix, comprising spectra of identified chemicals from the library, known interferent spectra, and the loadings of the background noise model; and the superscript "+" indicates the pseudoinverse of the matrix.

Referring to Equation 20, the number of factors used in Equation 20 is determined by the number of singular values in matrix K that are larger than the tolerance threshold (e.g., which can be calculated during run-time or preconfigured in the system). Based on the floating point in the matrix, the tolerance for the threshold to determine the rank of the matrix is defined as:

$$\text{Tolerance} = \max(m,n) \times \|K\| \times \epsilon$$

Equation 21 where:

$m = m_{Threat}$ (the number of threat chemicals) in $m_{Interferent}$ (the number of interferent chemicals) + $m_{sys}$ (the number of factors used for the color noise);

$\|K\|$ = the 2-norm of Matrix K; and $\epsilon$ = the smallest, floating point number that can be represented by the variable type used for Equation 21.

The accuracy of the estimated parameter vector, $C_{t+1}$, can be calculated:

$$\Sigma_{t+1} = \sigma_{t+1}^2 (K'K)^+ \qquad \text{Equation 22}$$

where:

$\Sigma_{t+1}$ = a matrix which characterizes the accuracy of $\hat{c}_{t+1}$;
K = the combined matrix, comprising sample spectra, interferent spectra, and the residual spectrum;
K' = the transponation of K; and
$\sigma_{t+1_{t+1}}^2$ = the root mean square (RMS) of the residual spectrum, calculated by:

$$\sigma_{t+1}^2 = \frac{(a_{t+1} - \hat{c}_{t+1}K)(a_{t+1} - \hat{c}_{t+1}K)'}{n - m - 1} \qquad \text{Equation 23}$$

where:

$a_{t+1}$ = the residual spectrum;
$\hat{c}_{t+1}$ = the estimated parameter vector;
K = the combined matrix, comprising sample spectra, interferent spectra, and the residual spectrum; and
m = total number of components, same as in Equation 21.

The search, detection, and quantification module 210 calculates, using Equation 23, an accuracy matrix for the estimated parameter vector based on the root mean square value. The search, detection, and quantification module 210 can calculate, for each digitized spectrum of each of the candidate chemicals, a root mean square. The estimated concentrations of the primary chemicals are the first $m_{Threat}$ elements of $\hat{c}_{t+1}$, denoted $\hat{c}_{i,t+1}$, i=1, 2, . . . , $m_{Threat}$. The variance of the estimated concentration is the matrix element, $\Sigma_{i,i}$ (i=1, 2, . . . $m_{Threat}$). The search, detection, and quantification module 210 can calculate a t-statistic, which can be used throughout the algorithm as a confidence metric (e.g., for calculating a primary chemical). The t-statistic can be calculated for each candidate chemical based on a variance of the associated candidate chemical. The t-statistic is given by:

$$t_{i,t+1} = \frac{c_{i,t+1}}{\sqrt{\Sigma_{i,i}}} \quad (i = 1, 2, \ldots, m_{threat}) \qquad \text{Equation 24}$$

where:

$t_{i,t+1}$ = the t-statistic for element i at time t+1;
$c_{i,t+1}$ = the concentration of element i at time t+1; and
$\Sigma_{i,i}$ = the variance of the estimated concentration of element i.

As described above, referring to Equations 18-24, the search, detection, and quantification module 210 refines the primary chemical calculation by calculating a residual analysis of the one or more library matrix entries based on a residual spectrum (e.g., $P_{sys}$) to generate an estimated parameter vector (e.g., $\hat{c}_{t+1}$). The search, detection, and quantification module 210 iteratively processes each candidate chemical using Equation 23 to calculate a RMS of each of the one or more chemicals. The search, detection, and quantification module 210 calculates, using Equation 24, a t-statistic for each of the chemicals. The t-statistic is based on a variance of the associated chemical of the one or more chemicals.

Referring to step 910, the search, detection, and quantification module 210 compares all of the RMS and t-statistics. The search, detection, and quantification module 210 retains the chemical (or multiple chemicals, depending how the detection system is configured) with the lowest RMS and highest t-statistic. The alarm module 224 can decide whether to indicate a detection and/or the alarm level based on the t-value.

Referring further to step 910, the search, detection, and quantification module 210 quantifies the one or more candidate chemicals based on the concentrations obtained from the least squares regression using Equation 20.

Advantageously, the first stage of the search, detection, and quantification process (e.g., described with reference to step 804 of FIG. 8) can quickly identify the one or more candidate chemicals. The second stage of the search, detection, and quantification process (e.g., described with reference to step 806 of FIG. 8) can then determine whether or not each of the candidate chemicals should be identified as a primary chemical. The data generated by the second stage can be used to determine whether to trigger an alarm (and to determine the level of the alarm).

An example is provided below to demonstrate the entire processes implemented by the detection system 10. A dataset from a real chemical test (collected on Dec. 2, 2008 at a national experiment test center) is given. In the experiment Cyanogen chloride (CK) was released 10 times at immediately dangerous to life or health (IDLH) concentrations (e.g., 20 ppm). The interferent of 1% headspace of Windex (NH3 and isopropyl alcohol (IPOH)) was introduced at the second 5 CK releases.

Figure 10:
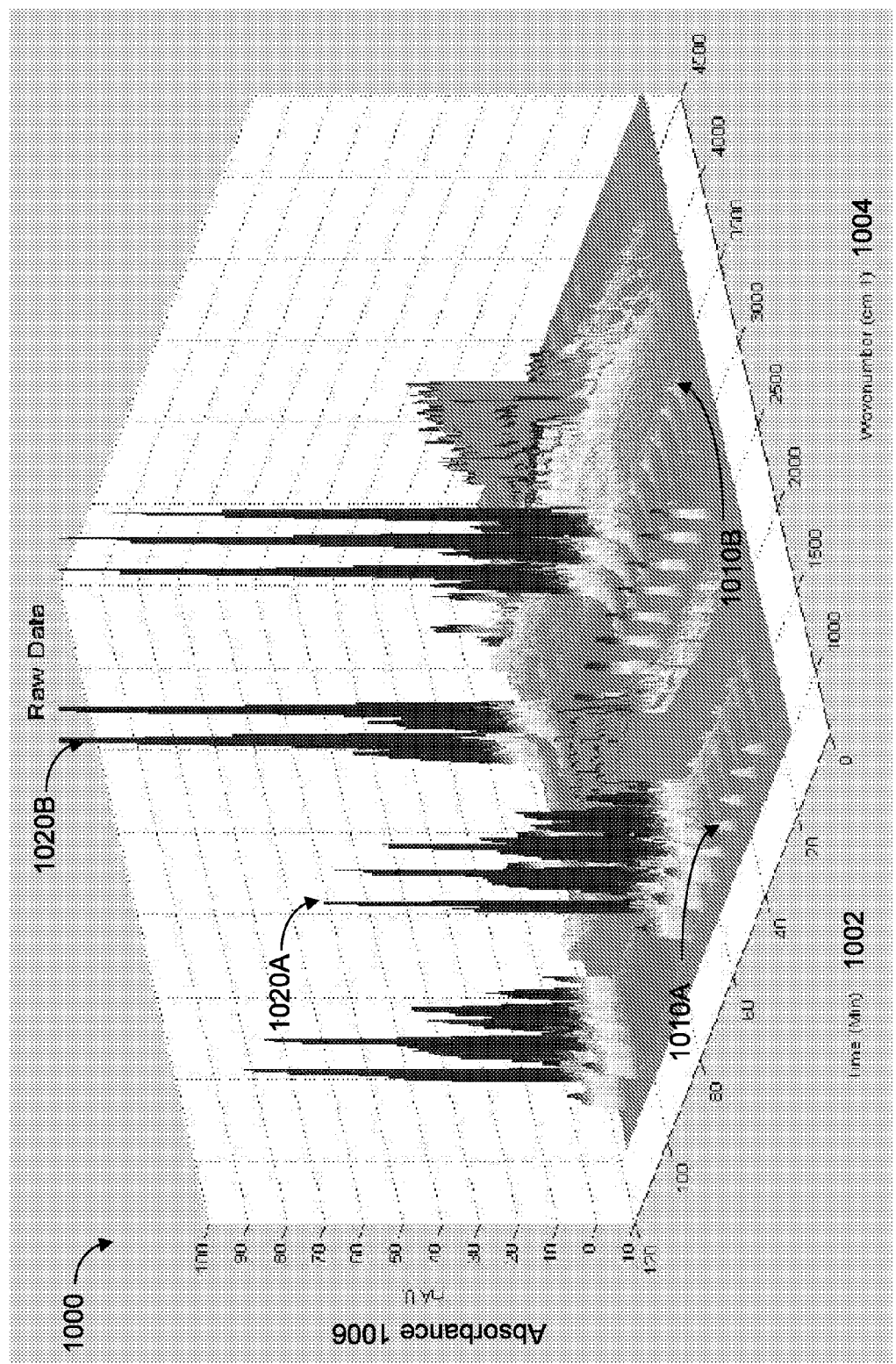
FIG. 10 illustrates an exemplary graph of test spectra measured using a single background spectrum.

FIG. 10 illustrates an exemplary graph 1000 of test spectra measured using a single background spectrum. The time axis 1002 is represented in minutes (min), spanning zero to 120 min (two hours). The wavenumber axis 1004 is represented in inverse centimeters (cm$^{-1}$), spanning from 1000 to 4500 cm$^{-1}$. The absorbance axis 1006 is represented in milli-Absorbance Units (mA.U.), spanning from −10 to 100. As shown in graph 1000, the CK peaks (1010A, 1010B) have been heavily interfered by big peaks of the NH3 and IPOH at second 5 chemical releases (second hour time frame, shown by 1020A, 1020B). The first spectrum from the experiment was employed as the background spectrum.

Figure 11:
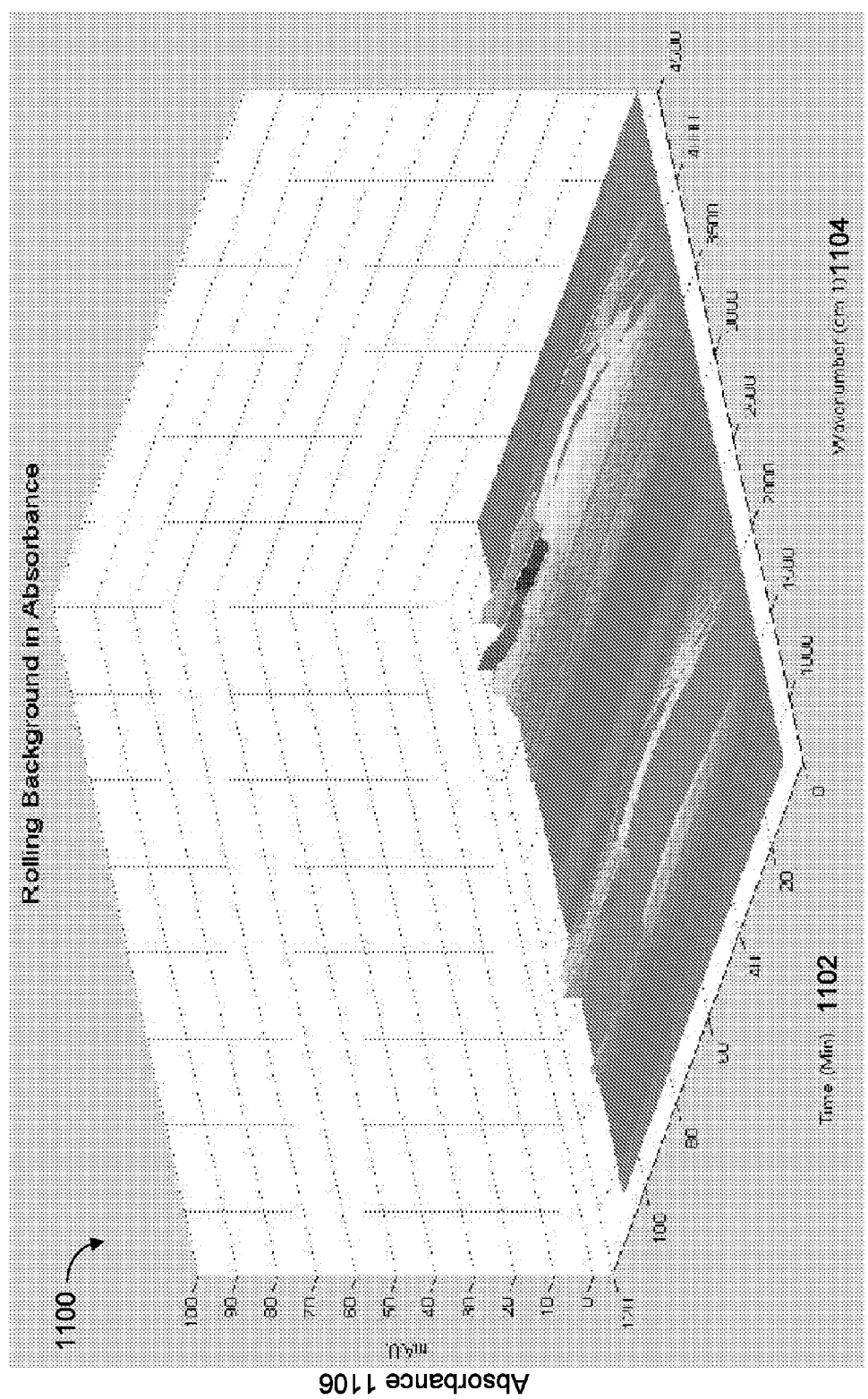
FIG. 11 illustrates an exemplary graph of an evolving background model calculated for the test spectra.

FIG. 11 illustrates an exemplary graph 1100 of a first model calculated for the test spectra. The time axis 1102 is represented in minutes (min), spanning zero to 120 min (two hours). The wavenumber axis 1104 is represented in inverse centimeters (cm$^{-1}$), spanning from 1000 to 4500 cm$^{-1}$. The absorbance axis 1106 is represented in milli-Absorbance Units (mA.U.), spanning from −10 to 100. The first model (in interferogram) was estimated according to Equation 4. The first model was then transferred into the frequency domain by Equation 5. Graph 1010 shows the absorbance spectra of the first model. As can be seen, about 5 mA.U. background has been estimated and removed.

Figure 12:
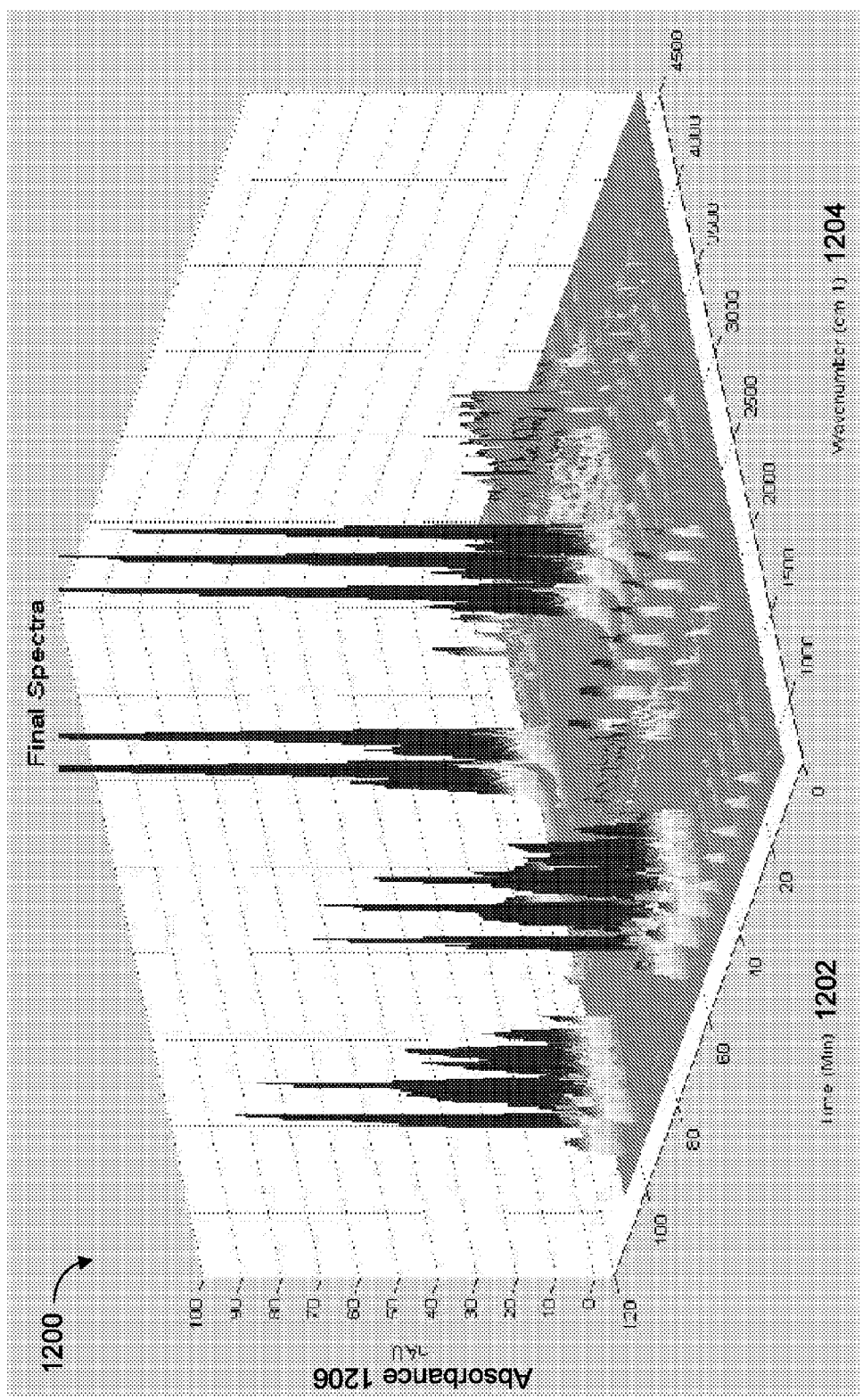
FIG. 12 illustrates an exemplary graph of test spectra measured using a multivariate multistage background model.

FIG. 12 illustrates an exemplary graph 1200 of test spectra measured using a background model. The time axis 1202 is represented in minutes (min), spanning zero to 120 min (two hours). The wavenumber axis 1204 is represented in inverse centimeters (cm$^{-1}$), spanning from 1000 to 4500 cm$^{-1}$. The absorbance axis 1206 is represented in milli-Absorbance Units (mA.U.), spanning from −10 to 100. For graph 1200, the second model was applied to remove the remaining background variation. The obtained final spectra illustrated in graph 1200 is properly corrected (e.g., and can be input into the search, detection, and quantification).

Figure 13:
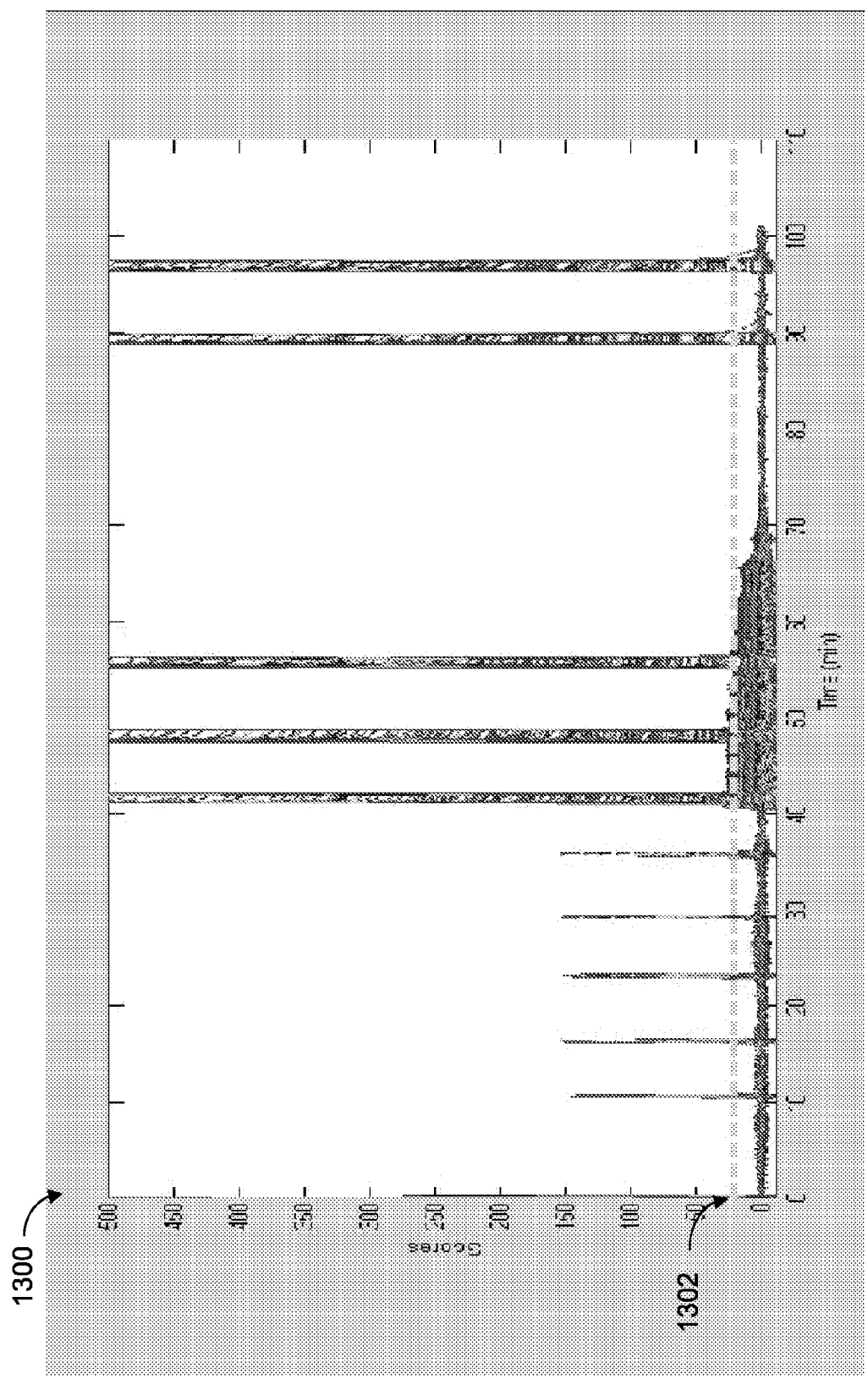
FIG. 13 illustrates an exemplary control chart for test spectra.

FIG. 13 illustrates an exemplary control chart 1300 for test spectra. The control hart 1300 was generated by applying the multivariate fault detection (Equations 11 through 15). The dash line 1302 is the threshold to detect the system changes. As shown by the lines extending above the threshold, the changes were identified as candidate chemicals. The candidate chemicals were then passed to the second stage of the fault detection and library search to calculate residual analysis (and determine the primary chemicals). The residual analysis was applied to identify the primary chemicals—the chemicals that were released (Equations 15 through 20). As described above, this is an iterative process. One chemical is identified and added into the equations each time. The process continues until either no sudden changes are detected or the maximum number of primary chemicals is reached.

The above-described systems and methods can be implemented in digital electronic circuitry, in computer hardware, firmware, and/or software. The implementation can be as a computer program product (i.e., a computer program tangibly embodied in an information carrier). The implementation can, for example, be in a machine-readable storage device, for execution by, or to control the operation of, data processing apparatus. The implementation can, for example, be a programmable processor, a computer, and/or multiple computers.

A computer program can be written in any form of programming language, including compiled and/or interpreted languages, and the computer program can be deployed in any form, including as a stand-alone program or as a subroutine, element, and/or other unit suitable for use in a computing environment. A computer program can be deployed to be executed on one computer or on multiple computers at one site.

Method steps can be performed by one or more programmable processors executing a computer program to perform functions of the invention by operating on input data and generating output. Method steps can also be performed by and an apparatus can be implemented as special purpose logic circuitry. The circuitry can, for example, be a FPGA (field programmable gate array) and/or an ASIC (application-specific integrated circuit). Modules, subroutines, and software agents can refer to portions of the computer program, the processor, the special circuitry, software, and/or hardware that implements that functionality.

Processors suitable for the execution of a computer program include, by way of example, both general and special purpose microprocessors, and any one or more processors of any kind of digital computer. Generally, a processor receives instructions and data from a read-only memory or a random access memory or both. The essential elements of a computer are a processor for executing instructions and one or more memory devices for storing instructions and data. Generally, a computer can include, can be operatively coupled to receive data from and/or transfer data to one or more mass storage devices for storing data (e.g., magnetic, magneto-optical disks, or optical disks).

Data transmission and instructions can also occur over a communications network. Information carriers suitable for embodying computer program instructions and data include all forms of non-volatile memory, including by way of example semiconductor memory devices. The information carriers can, for example, be EPROM, EEPROM, flash memory devices, magnetic disks, internal hard disks, removable disks, magneto-optical disks, CD-ROM, and/or DVD-ROM disks. The processor and the memory can be supplemented by, and/or incorporated in special purpose logic circuitry.

To provide for interaction with a user, the above described techniques can be implemented on a computer having a display device. The display device can, for example, be a cathode ray tube (CRT) and/or a liquid crystal display (LCD) monitor. The interaction with a user can, for example, be a display of information to the user and a keyboard and a pointing device (e.g., a mouse or a trackball) by which the user can provide input to the computer (e.g., interact with a user interface element). Other kinds of devices can be used to provide for interaction with a user. Other devices can, for example, be feedback provided to the user in any form of sensory feedback (e.g., visual feedback, auditory feedback, or tactile feedback). Input from the user can, for example, be received in any form, including acoustic, speech, and/or tactile input.

The above described techniques can be implemented in a distributed computing system that includes a back-end component. The back-end component can, for example, be a data server, a middleware component, and/or an application server. The above described techniques can be implemented in a distributing computing system that includes a front-end component. The front-end component can, for example, be a client computer having a graphical user interface, a Web browser through which a user can interact with an example implementation, and/or other graphical user interfaces for a transmitting device. The components of the system can be interconnected by any form or medium of digital data communication (e.g., a communication network). Examples of communication networks include a local area network (LAN), a wide area network (WAN), the Internet, wired networks, and/or wireless networks.

The system can include clients and servers. A client and a server are generally remote from each other and typically interact through a communication network. The relationship of client and server arises by virtue of computer programs running on the respective computers and having a client-server relationship to each other.

Packet-based networks can include, for example, the Internet, a carrier internet protocol (IP) network (e.g., local area network (LAN), wide area network (WAN), campus area network (CAN), metropolitan area network (MAN), home area network (HAN)), a private IP network, an IP private branch exchange (IPBX), a wireless network (e.g., radio access network (RAN), 802.11 network, 802.16 network, general packet radio service (GPRS) network, HiperLAN), and/or other packet-based networks. Circuit-based networks can include, for example, the public switched telephone network (PSTN), a private branch exchange (PBX), a wireless network (e.g., RAN, bluetooth, code-division multiple access (CDMA) network, time division multiple access (TDMA) network, global system for mobile communications (GSM) network), and/or other circuit-based networks.

The transmitting device can include, for example, a computer, a computer with a browser device, a telephone, an IP phone, a mobile device (e.g., cellular phone, personal digital assistant (PDA) device, laptop computer, electronic mail device), and/or other communication devices. The browser device includes, for example, a computer (e.g., desktop computer, laptop computer) with a world wide web browser (e.g., Microsoft® Internet Explorer® available from Microsoft Corporation, Mozilla® Firefox available from Mozilla Corporation). The mobile computing device includes, for example, a personal digital assistant (PDA).

Comprise, include, and/or plural forms of each are open ended and include the listed parts and can include additional parts that are not listed. And/or is open ended and includes one or more of the listed parts and combinations of the listed parts.

One skilled in the art will realize the invention may be embodied in other specific forms without departing from the spirit or essential characteristics thereof. The foregoing embodiments are therefore to be considered in all respects illustrative rather than limiting of the invention described herein. Scope of the invention is thus indicated by the appended claims, rather than by the foregoing description, and all changes that come within the meaning and range of equivalency of the claims are therefore intended to be embraced therein.

What is claimed is:

1. A computerized method for detecting and quantifying chemicals in a continuously sampled liquid or gas sample stream, comprising:
    receiving, by a computing device, a sample measurement comprising a digitized spectroscopic profile;
    calculating, by the computing device, a multivariate multistage background model comprising a first model that models a first time effect, a second model that models a second time effect that is different than the first time effect, or both;
    generating, by the computing device, a background corrected sample measurement based on the sample measurement and the multivariate multistage background model; and
    executing, by the computing device, a multivariate multistage library search, fault detection, and quantification algorithm to identify one or more primary chemicals in the background corrected sample measurement, the algorithm comprising:
        identifying one or more candidate chemicals in the background corrected sample measurement based on a multivariate statistical process control in comparison of the background corrected sample measurement to a spectral reference library;
        performing at least one of (i) identifying a first primary chemical based on a focused chemical evaluation of the one or more candidate chemicals or (ii) quantifying the first primary chemical based on the focused chemical evaluation of the one or more candidate chemicals;
        calculating a residual profile by subtracting the first primary chemical from the background corrected sample measurement; and
        identifying a second set of one or more candidate chemicals in the residual profile based on a comparison of the residual profile to the spectral reference library.

2. The method of claim 1, wherein identifying the first primary chemical comprises determining there are zero primary chemicals.

3. The method of claim 1, wherein calculating comprises updating the multivariate multistage background model.

4. The method of claim 1, wherein the multivariate multistage library search, fault detection, and quantification algorithm further comprises:
    quantifying content by estimating the first primary chemical concentration from the background corrected sample measurement; and
    identifying a second primary chemical based on a focused chemical evaluation of the second set of one or more candidate chemicals.

5. The method of claim 1, further comprising:
    determining the sample measurement is suitable for inclusion into the multivariate multistage background model; and
    updating the multivariate multistage background model based on the sample measurement.

6. The method of claim 5, further comprising filtering the sample measurement through a data buffer to prevent contamination resulting from slow chemical data poisoning in the sample stream.

7. The method of claim 6, wherein a size of the data buffer is determined based on a data poisoning rate value.

8. The method of claim 5, further comprising reducing an influence of one or more interference chemicals in the sample measurement based on a mask function.

9. The method of claim 8, further comprising:
    identifying one or more chemical interferents; and
    updating the mask function based on one or more identified chemical interferents.

10. The method of claim 5, further comprising defining one or more update conditions, comprising:
    updating at least one of (i) the multivariate multistage background model or (ii) the multivariate multistage library search, fault detection, and quantification model, if zero chemical compounds are detected in the sample measurement;
    updating at least one of (i) the multivariate multistage background model or (ii) the multivariate multistage library search, fault detection, and quantification model, if zero interest chemical compounds are detected in the sample measurement;
    updating at least one of (i) the multivariate multistage background model or (ii) the multivariate multistage library search, fault detection, and quantification model, if there is no alarm of any interest chemical compounds in the sample measurement; or
    not updating at least one of (i) the multivariate multistage model or (ii) the multivariate multistage library search, fault detection, and quantification model.

11. A system for detecting and quantifying chemicals in a continuously sampled liquid or gas sample stream, comprising:
    a data acquisition module configured to receive a sample measurement comprising a digitized spectroscopic profile;
    a multivariate multistage background module in communication with the data acquisition module configured to:
        calculate a multivariate multistage background model comprising a first model that models a first time effect, a second model that models a second time effect that is different than the first time effect, or both;
        generate a background corrected sample measurement based on the sample measurement and the multivariate multistage background model; and
    a multivariate multistage library search, fault detection, and quantification module in communication with the data acquisition module and the multivariate multistage background module configured to execute a multivariate multistage library search, fault detection, and quantification algorithm to identify one or more primary chemicals in the background corrected sample measurement, configured to:
        identify one or more candidate chemicals in the background corrected sample measurement based on a comparison of the background corrected sample measurement to a spectral reference library;
        perform at least one of (i) identifying a first primary chemical based on a focused chemical evaluation of the one or more candidate chemicals or (ii) quantifying the first primary chemical based on the focused chemical evaluation of the one or more candidate chemicals;

calculate a residual profile by subtracting the first primary chemical from the background corrected sample measurement; and identify a second set of one or more candidate chemicals in the residual profile based on a comparison of the residual profile to the spectral reference library.

12. A non-transitory computer readable medium containing computer instructions stored therein for causing a data processing apparatus to:

receive a sample measurement comprising a digitized spectroscopic profile;

calculate a multivariate multistage background model comprising a first model that models a first time effect, a second model that models a second time effect that is different than the first time effect, or both;

generate a background corrected sample measurement based on the sample measurement and the multivariate multistage background model; and execute a multivariate multistage library search, fault detection, and quantification algorithm to identify one or more primary chemicals in the background corrected sample measurement, the algorithm being configured to:

identify one or more candidate chemicals in the background corrected sample measurement based on a multivariate statistical process control in comparison of the background corrected sample measurement to a spectral reference library;

identify a first primary chemical based on a focused chemical evaluation of the one or more candidate chemicals;

calculate a residual profile by subtracting the first primary chemical from the background corrected sample measurement; and identify a second set of one or more candidate chemicals in the residual profile based on a comparison of the residual profile to the spectral reference library.

* * * * *